United States Patent
Finley et al.

(10) Patent No.: US 9,510,771 B1
(45) Date of Patent: Dec. 6, 2016

(54) SYSTEMS AND METHODS FOR PERFORMING SPINE SURGERY

(71) Applicant: NuVasive, Inc., San Diego, CA (US)

(72) Inventors: Eric Finley, Poway, CA (US); Albert Kim, San Diego, CA (US); Thomas Scholl, San Diego, CA (US); Jeffrey Barnes, San Diego, CA (US); Bryce Nesbitt, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/663,459

(22) Filed: Oct. 29, 2012

Related U.S. Application Data

(60) Provisional application No. 61/671,537, filed on Jul. 13, 2012, provisional application No. 61/552,466, filed on Oct. 28, 2011.

(51) Int. Cl.
*A61B 5/06* (2006.01)

(52) U.S. Cl.
CPC .................................... *A61B 5/061* (2013.01)

(58) Field of Classification Search
CPC .... A61B 5/06; A61B 5/066; A61B 19/5244; A61B 2019/5251; A61B 2019/5289
USPC ........... 378/21; 600/407, 424, 427; 700/264; 606/99, 104, 130
See application file for complete search history.

(56) References Cited

U.S. PATENT DOCUMENTS

| | | | |
|---|---|---|---|
| 5,189,690 A | 2/1993 | Samuel | |
| 5,283,808 A | 2/1994 | Cramer | |
| 5,661,775 A | 8/1997 | Cramer | |
| 5,772,594 A | 6/1998 | Barrick | |
| 5,823,960 A | 10/1998 | Young | |
| 5,835,562 A | 11/1998 | Ramsdell | |
| 6,050,724 A | 4/2000 | Schmitz | |
| 6,079,876 A | 6/2000 | Schuetz | |
| 6,226,548 B1 | 5/2001 | Foley | |
| 6,235,038 B1 | 5/2001 | Hunter | |
| 6,236,875 B1 | 5/2001 | Bucholz | |
| 6,266,394 B1 | 7/2001 | Marino | |
| 6,267,502 B1 | 7/2001 | McNeirney | |
| 6,285,902 B1 | 9/2001 | Kienzle | |
| 6,340,363 B1 | 1/2002 | Bolger | |
| 6,347,240 B1 | 2/2002 | Foley | |
| 6,379,041 B1 | 4/2002 | Schuetz | |
| 6,470,207 B1 | 10/2002 | Simon | |
| 6,490,477 B1 | 12/2002 | Zylka | |
| 6,519,319 B1 | 2/2003 | Marino | |
| 6,527,443 B1 | 3/2003 | Vilsmeier | |
| 6,533,455 B2 | 3/2003 | Graumann | |
| 6,542,770 B2 | 4/2003 | Zylka | |
| 6,608,884 B1 | 8/2003 | Mazess | |
| 6,697,664 B2 | 2/2004 | Kienzle | |
| 6,701,174 B1 | 3/2004 | Krause | |
| 6,714,629 B2 | 3/2004 | Vilsmeier | |
| 6,714,810 B2 | 3/2004 | Grzeszczuk | |
| 6,776,526 B2 | 8/2004 | Zeiss | |
| 6,804,547 B2 | 10/2004 | Pelzer | |

(Continued)

FOREIGN PATENT DOCUMENTS

| | | |
|---|---|---|
| DE | 102011006562 | 10/2012 |
| DE | 102011114332 | 3/2013 |

(Continued)

*Primary Examiner* — Michael Rozanski
(74) *Attorney, Agent, or Firm* — Stephen H. Hall; Bradley Arant Boult Cummings LLP

(57) ABSTRACT

The present application includes a position tracking system for tracking the location of surgical objects within the surgical field, a neuromonitoring system for detecting the existence of (and optionally the distance and/or direction to) neural structures during a surgical procedure, and a processing system communicatively linked to both the position tracking system and the neuromonitoring system.

18 Claims, 25 Drawing Sheets

(56) References Cited

U.S. PATENT DOCUMENTS

| | | |
|---|---|---|
| 6,817,762 B2 | 11/2004 | Proksa |
| 6,851,855 B2 | 2/2005 | Mitschke |
| 6,925,319 B2 | 8/2005 | McKinnon |
| 6,932,506 B2 | 8/2005 | Mitschke |
| 6,947,786 B2 | 9/2005 | Simon |
| 6,978,166 B2 | 12/2005 | Foley |
| 7,010,080 B2 | 3/2006 | Mitschke |
| 7,035,371 B2 | 4/2006 | Boese |
| 7,117,027 B2 | 10/2006 | Zheng |
| 7,125,165 B2 | 10/2006 | Lütjens |
| 7,139,601 B2 | 11/2006 | Bucholz |
| 7,167,738 B2 | 1/2007 | Schweikard |
| 7,251,522 B2 | 7/2007 | Essenreiter |
| 7,324,626 B2 | 1/2008 | Vilsmeier |
| RE40,176 E | 3/2008 | Peshkin |
| 7,391,846 B2 | 6/2008 | Verdonck |
| 7,450,743 B2 | 11/2008 | Sundar |
| 7,508,388 B2 | 3/2009 | Barfuss |
| 7,519,415 B2 | 4/2009 | Mitschke |
| 7,567,834 B2 | 7/2009 | Clayton |
| 7,570,791 B2 | 8/2009 | Frank |
| 7,570,987 B2 | 8/2009 | Raabe |
| 7,587,076 B2 | 9/2009 | Kraus |
| 7,587,235 B2 | 9/2009 | Wist |
| 7,590,440 B2 | 9/2009 | Lau |
| 7,590,442 B2 | 9/2009 | Boese |
| 7,603,155 B2 | 10/2009 | Jensen |
| 7,603,163 B2 | 10/2009 | McNeirney |
| 7,630,753 B2 | 12/2009 | Simon |
| 7,657,075 B2 | 2/2010 | Viswanathan |
| 7,677,801 B2 | 3/2010 | Pakzaban |
| 7,689,014 B2 | 3/2010 | Abovitz |
| 7,689,019 B2 | 3/2010 | Boese |
| 7,689,042 B2 | 3/2010 | Brunner |
| 7,693,565 B2 | 4/2010 | Shai |
| 7,756,567 B2 | 7/2010 | Kuduvalli |
| 7,764,984 B2 | 7/2010 | Desmedt |
| 7,778,690 B2 | 8/2010 | Boese |
| 7,787,932 B2 | 8/2010 | Vilsmeier |
| 7,801,342 B2 | 9/2010 | Boese |
| 7,804,991 B2 | 9/2010 | Abovitz |
| 7,831,294 B2 | 11/2010 | Viswanathan |
| 7,835,778 B2 * | 11/2010 | Foley et al. .................. 600/407 |
| 7,835,784 B2 | 11/2010 | Mire |
| 7,873,403 B2 | 1/2011 | Lachner |
| RE42,194 E | 3/2011 | Foley |
| 7,922,391 B2 | 4/2011 | Essenreiter |
| 7,953,471 B2 | 5/2011 | Clayton |
| 7,970,190 B2 | 6/2011 | Steinle |
| 7,974,677 B2 | 7/2011 | Mire |
| 7,995,827 B2 | 8/2011 | Wagner |
| 7,996,064 B2 | 8/2011 | Simon |
| 8,010,177 B2 | 8/2011 | Csavoy |
| 8,045,677 B2 | 10/2011 | Movassaghi |
| 8,055,046 B2 | 11/2011 | Feilkas |
| 8,090,174 B2 | 1/2012 | Navab |
| 8,104,958 B2 | 1/2012 | Weiser |
| 8,106,905 B2 | 1/2012 | Markowitz |
| 8,126,111 B2 | 2/2012 | Uhde |
| 8,165,660 B2 | 4/2012 | Pfister |
| 8,180,130 B2 | 5/2012 | Sebok |
| 8,238,631 B2 | 8/2012 | Hartmann |
| 8,244,064 B2 | 8/2012 | Boese |
| 8,275,445 B2 | 9/2012 | Berting |
| 8,301,220 B2 | 10/2012 | Basterrechea et al. |
| 8,374,678 B2 | 2/2013 | Graumann |
| 8,457,373 B2 | 6/2013 | Kamen |
| 8,463,005 B2 | 6/2013 | Erbel |
| 8,483,434 B2 | 7/2013 | Buehner |
| 8,503,745 B2 | 8/2013 | Simon |
| 8,554,307 B2 | 10/2013 | Razzaque |
| 8,585,598 B2 | 11/2013 | Razzaque |
| 8,600,138 B2 | 12/2013 | Gorges |
| 8,600,478 B2 | 12/2013 | Verard |
| 8,634,896 B2 | 1/2014 | Sra |
| 8,641,621 B2 | 2/2014 | Razzaque |
| 8,694,075 B2 | 4/2014 | Groszmann |
| 2001/0011175 A1 | 8/2001 | Hunter |
| 2001/0053204 A1 | 12/2001 | Navab |
| 2002/0032375 A1 | 3/2002 | Bauch |
| 2002/0077543 A1 | 6/2002 | Grzeszczuk |
| 2002/0085681 A1 | 7/2002 | Jensen |
| 2002/0172328 A1 | 11/2002 | Dekel |
| 2003/0181809 A1 | 9/2003 | Hall |
| 2004/0077939 A1 | 4/2004 | Graumann |
| 2004/0171924 A1 | 9/2004 | Mire |
| 2005/0004449 A1 | 1/2005 | Mitschke |
| 2005/0027193 A1 | 2/2005 | Mitschke |
| 2005/0059886 A1 | 3/2005 | Webber |
| 2005/0119561 A1 | 6/2005 | Kienzle |
| 2005/0165292 A1 | 7/2005 | Simon |
| 2005/0203386 A1 | 9/2005 | Heigl |
| 2006/0025681 A1 | 2/2006 | Abovitz |
| 2006/0036162 A1 | 2/2006 | Shahidi |
| 2006/0122483 A1 | 6/2006 | Foley |
| 2006/0293582 A1 | 12/2006 | Jensen |
| 2007/0016005 A1 | 1/2007 | Timinger |
| 2007/0173717 A1 | 7/2007 | Camus |
| 2007/0238986 A1 | 10/2007 | Graumann |
| 2007/0242869 A1 | 10/2007 | Luo |
| 2008/0147086 A1 | 6/2008 | Pfister |
| 2008/0177176 A1 | 7/2008 | Basterrechea |
| 2008/0285724 A1 | 11/2008 | Dehler |
| 2008/0306378 A1 | 12/2008 | Trousset |
| 2008/0312528 A1 | 12/2008 | Bertolina |
| 2009/0074139 A1 | 3/2009 | Hempel |
| 2009/0135191 A1 | 5/2009 | Azar |
| 2009/0143788 A1 | 6/2009 | Fang |
| 2009/0234217 A1 | 9/2009 | Mire |
| 2009/0262111 A1 | 10/2009 | Simon |
| 2009/0290771 A1 | 11/2009 | Frank |
| 2010/0016712 A1 | 1/2010 | Bartal |
| 2010/0041985 A1 | 2/2010 | Simon |
| 2010/0067773 A1 | 3/2010 | Yamaguchi |
| 2010/0106010 A1 | 4/2010 | Rubner |
| 2010/0239152 A1 | 9/2010 | Furst |
| 2010/0290690 A1 | 11/2010 | Hartmann |
| 2010/0292565 A1 | 11/2010 | Meyer |
| 2010/0295931 A1 | 11/2010 | Schmidt |
| 2011/0054293 A1 | 3/2011 | Markowitz |
| 2011/0054308 A1 | 3/2011 | Cohen |
| 2011/0071389 A1 | 3/2011 | Simon |
| 2011/0213379 A1 | 9/2011 | Blau et al. |
| 2011/0268248 A1 | 11/2011 | Simon |
| 2011/0276179 A1 * | 11/2011 | Banks et al. .................. 700/264 |
| 2011/0282189 A1 | 11/2011 | Graumann |
| 2012/0008741 A1 | 1/2012 | Hendriks |
| 2012/0188352 A1 | 7/2012 | Wittenberg |
| 2012/0259204 A1 | 10/2012 | Carrat |
| 2013/0051647 A1 | 2/2013 | Miao |
| 2013/0066196 A1 | 3/2013 | Graumann |
| 2013/0172732 A1 | 7/2013 | Kiraly |
| 2013/0245477 A1 | 9/2013 | Brodnick |
| 2013/0253312 A1 | 9/2013 | Sato |
| 2013/0314440 A1 | 11/2013 | Simon |
| 2013/0324839 A1 | 12/2013 | Chien |
| 2014/0049629 A1 | 2/2014 | Siewerdsen |
| 2014/0114180 A1 | 4/2014 | Jain |
| 2014/0140598 A1 | 5/2014 | Lu |
| 2014/0171962 A1 | 6/2014 | Kang |
| 2014/0180062 A1 | 6/2014 | Amit |

FOREIGN PATENT DOCUMENTS

| | | |
|---|---|---|
| DE | 102011114333 | 3/2013 |
| DE | 102012200536 | 6/2013 |
| WO | WO-2013/102827 | 7/2013 |
| WO | WO-2013/156893 | 10/2013 |

* cited by examiner

FIG. 9

SYSTEMS AND METHODS FOR PERFORMING SPINE SURGERY

CROSS-REFERENCE TO RELATED APPLICATIONS

This patent application claims priority to U.S. Provisional Application Ser. No. 61/552,466 filed on Oct. 28, 2011 and U.S. Provisional Application Ser. No. 61/671,537 filed on Jul. 13, 2012, the complete disclosures of which are hereby incorporated by reference into this application as if set forth fully herein.

FIELD

The present application pertains to spine surgery. More particularly, the present application pertains to a surgical tracking system that monitors the locations of surgical objects and nerves within the body during spine surgery.

BACKGROUND

The spinal column is a highly complex system of bones and connective tissues that provide support for the body and protect the delicate spinal cord and nerves. The spinal column includes a series of vertebral bodies stacked atop one another, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies. The spine has a natural curvature (i.e., lordosis in the lumbar and cervical regions and kyphosis in the thoracic region) such that the endplates of the upper and lower vertebrae are inclined towards one another.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease, or trauma (such as ruptured or slipped discs, degenerative disc disease, fractured vertebrae, and the like). Patients that suffer from such conditions often experience extreme and debilitating pain, as well as diminished nerve function.

A noteworthy trend in the medical community is the move away from performing surgery via traditional "open" techniques in favor of so-called "minimally invasive" or "minimal access" techniques. Open surgical techniques are generally undesirable in that they typically require large incisions with high amounts of tissue displacement to gain access to the surgical target site, which produces concomitantly high amounts of pain, lengthened hospitalization (increasing health care costs), and high morbidity in the patient population. Less-invasive surgical techniques (including minimal access and minimally invasive techniques are gaining favor due to the fact that they involve accessing the surgical target site via incisions of substantially smaller size with greatly reduced tissue displacement requirements. This, in turn, reduces the pain, morbidity, and cost associated with such procedures.

One disadvantage to performing minimally invasive surgery is the increased reliance on radiographic imaging to "see" the spinal target site, instruments, and implants during the surgery. While this increased exposure is generally negligible for the patient, over time and over multiple procedures on different patients, this increased exposure adds up for the surgeon and other operating room personnel. Systems and methods have been developed to reduce reliance on radiographic imaging during spine surgery. Once such system and method involves three-dimensional (3D) navigation systems that use positional tracking systems to track the position of implants and instruments relative to the spinal target site and present the surgeon with a representative image of the instrument superimposed on an image of the target site to indicate the position of the implant or instrument relative to the anatomical structures depicted in the image. (e.g. spinal target site). However, these systems have the disadvantages of generally requiring that reference markers be somehow fixed to the patient (e.g. anchoring a pin or other instrument into the patient's spine, thus causing additional trauma to the patient's anatomy), requiring input of pre-operative CT images into the system before or during the procedure, and/or requiring large, specialized, and expensive equipment that may not be available in certain instances or operating rooms. Furthermore, even though 3D navigation provides spatial information regarding a target surgical site, instruments, and implants during surgery, it does not provide neurophysiologic information regarding the nerves lying near and around the operative corridor.

A need exists for systems and methods that provide both information regarding the target spine site, surgical implants, instruments, and nerves surrounding the operative corridor during minimally-invasive spine surgeries. The systems and methods described herein are directed to addressing the challenges described above, and others, associated with various minimally-invasive spine procedures.

SUMMARY

The present invention includes a system and methods for decreased reliance on fluoroscopic imaging while avoiding harm to neural tissue during surgery. According to a broad aspect, the present invention includes a position tracking system for tracking the location of surgical objects within the surgical field, a neuromonitoring system for detecting the existence of (and optionally the distance and/or direction to) neural structures during a surgical procedure, and a processing system communicatively linked to both the position tracking system and the neuromonitoring system.

According to another aspect of the present invention, the position tracking system includes an infrared (IR) position sensor, an IR-reflective tracking array attached to an intraoperative imaging system, and at least one IR-reflective tracking array attached to at least one surgical object. The position tracking system is communicatively linked to the processing system such that the processing system may display position tracking information to a user (e.g., a surgeon or a medical professional assisting the surgeon).

According to another aspect of the present invention, the neuromonitoring system includes instruments capable of stimulating the peripheral nerves of a patient and additional instruments capable of recording the evoked neuromuscular responses. The neuromonitoring system is communicatively linked to the processing system such that the processing unit is programmed to measure the response of nerves depolarized by the stimulation signals to indicate the existence of (and optionally the distance and/or direction to neural structures during the surgical procedure.

According to another aspect of the present invention, the processing system is programmed to perform a plurality of predetermined functions using one or both of the position tracking system and neuromonitoring system. For example, the processing system may be programmed to register the position of a patient, scale virtual fluoroscopic images, track one or more surgical objects within the patient, determine the distance between two points of interest within the surgical field, determine the angle between two points of interest within the surgical field, recommend the size of one or more surgical instruments or implants, perform neurophysiologic monitoring, map neurophysiologic monitoring onto virtual fluoroscopic images, correct for translational and/or rotational offsets of virtual fluoroscopic images, and track the movement of one or more reference objects during the surgical procedure. The processing system is further configured to display the results of these predetermined functions to the user in a meaningful way.

According to another aspect of the invention, one or more surgical procedures may be performed using various embodiments of the system. According to one embodiment, the surgical procedure is a minimally-invasive lateral lumbar surgery. According to another embodiment, the surgical procedure is a posterior (open or minimally invasive) lumbar surgery.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 9 is a screen shot depicting an example IR positioning sensor setup screen of the system of FIG. 1;

DESCRIPTION OF THE PREFERRED EMBODIMENT

Figure 1:
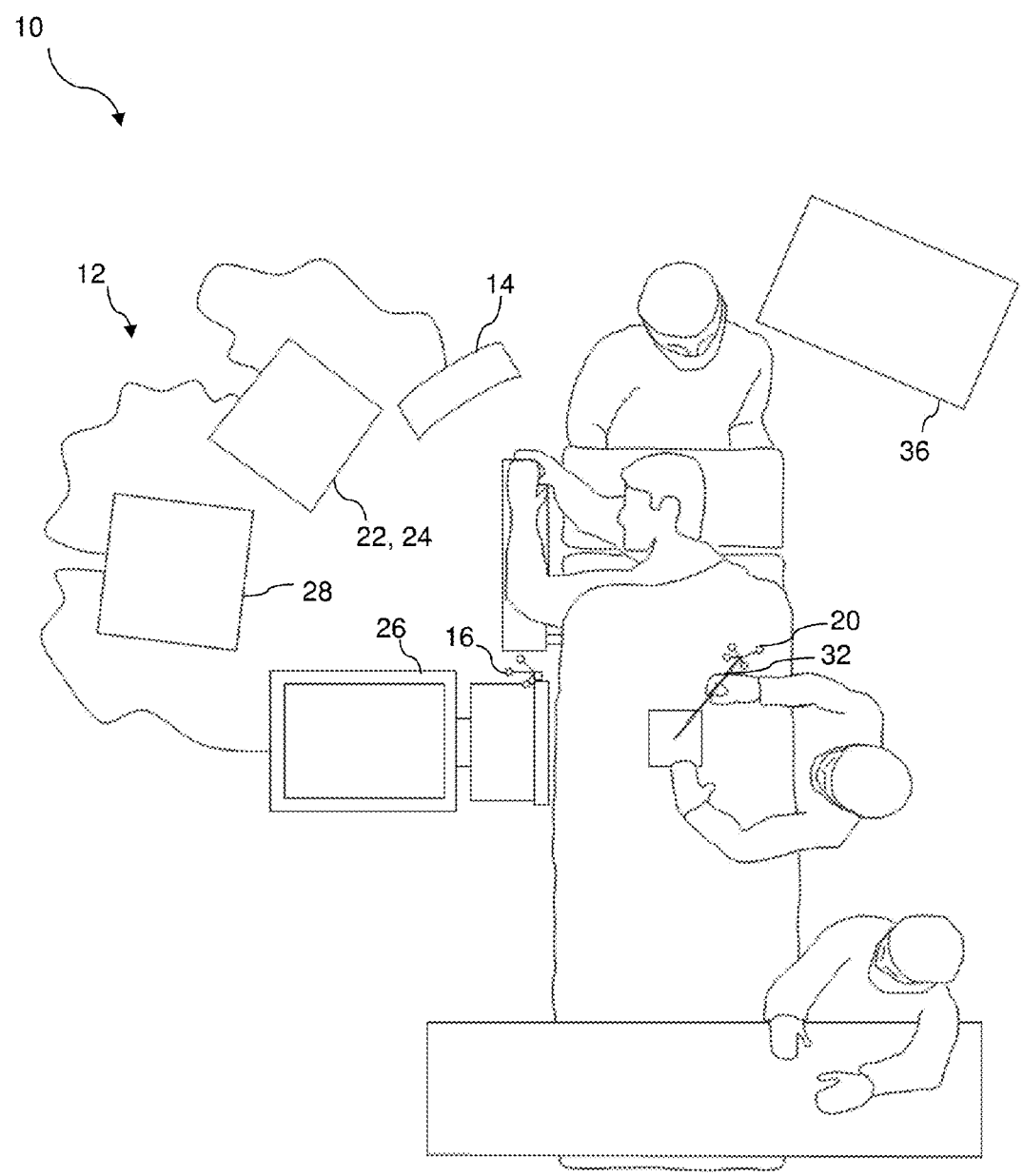
FIG. 1 is an example operating room setup depicting the components of a surgical tracking system, according to an example embodiment.

Illustrative embodiments of the invention are described below. In the interest of clarity, not all features of an actual implementation are described in this specification. It will of course be appreciated that in development of any such actual embodiment, numerous implantation-specific decisions must be made to achieve the developers' specific goals such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods disclosed herein boast a variety of inventive features and components that warrant patent protection, both individually and in combination.

The present invention includes a surgical tracking system that monitors the 3D location of objects in or near a surgical field and then conveys the position of these objects to a user relative to traditional, yet virtual anatomical views. The system conveys the position of virtualized representations of these surgical objects over one or more virtual fluoroscopic images. The virtual surgical objects may be generated with software (e.g., 3D CAD models) and then superimposed onto static two-dimensional (2D) images (e.g., in lateral and anterior-posterior (A/P) views). The user may rely on these images to locate the surgical objects relative to the patient's anatomy instead of taking repeated x-ray images. While the system does not eliminate the need for fluoroscopic imaging entirely, it does limit the number of fluoroscopic images required during a surgical procedure thereby minimizing the amount of ionizing radiation that the patient and user are exposed to. Furthermore, the system accomplishes this reduction in radiation exposure without requiring reference markers fixed to the patient, input of pre-operative CT images, or additional large, specialized, and costly equipment.

Various embodiments are described of the surgical tracking system and surgical uses thereof for enhancing the safety and efficiency of surgical procedures. In one example, the present invention may facilitate monitoring the location and orientation of surgical access instruments which can aid in both the insertion and positioning of the surgical access instruments themselves, as well as aiding in the later insertion of instruments and/or implants through the surgical access instruments. In another example, tracking the location of surgical instruments within the surgical field may be accomplished with significantly decreased reliance on intraoperative imaging. In yet another example, the present invention may be used in conjunction with, or integrated into, a neuromonitoring system for assessing one or more of nerve proximity (and/or nerve directionality) and pedicle integrity, among other functions. In still another example, the present invention may facilitate safe and reproducible pedicle screw placement by monitoring the trajectory of various surgical instruments used during pilot hole formation and/or screw insertion. While the above examples are described in more detail below, it is expressly noted that they are set forth by way of example and that the present invention may be suitable for use in any number of additional surgical actions where tracking the 3D location of surgical instruments and implants within the surgical field and decreased exposure to x-ray radiation are desired. Accordingly, it will be appreciated then that while the surgical tracking system is generally discussed herein as being attached to instruments such as dilating cannulas, tissue retractors, C-arms, pedicle access tools, etc., other instruments may be substituted depending on the surgical procedure being performed and/or the needs of the surgeon.

With reference now to FIG. 1, there is shown, by way of example, one embodiment of a surgical tracking system 10 including a position tracking system 12 and at least one surgical object to be tracked. Preferably, the position tracking system 12 includes an infrared (IR) position sensor 14 (also referred to as an "IR camera"), an IR-reflective tracking array 16 mounted on an intraoperative imaging system 18, an IR-reflective tracking array 20 mountable to each surgical object to be tracked (e.g. initial dilator 32) and a feedback and control device comprising a control unit 22 and a display 24. The control unit 22 has position tracking software and C-arm video import capabilities and is communicatively linked to the display 24 so that information relevant to the surgical procedure may be conveyed to the user in a meaningful manner. By way of example, the relevant information includes, but is not limited to, spatial positioning data (e.g., translational data in the x, y, and z axes and orientation/rotational data) acquired by the IR position tracking sensor 14.

Figure 2:
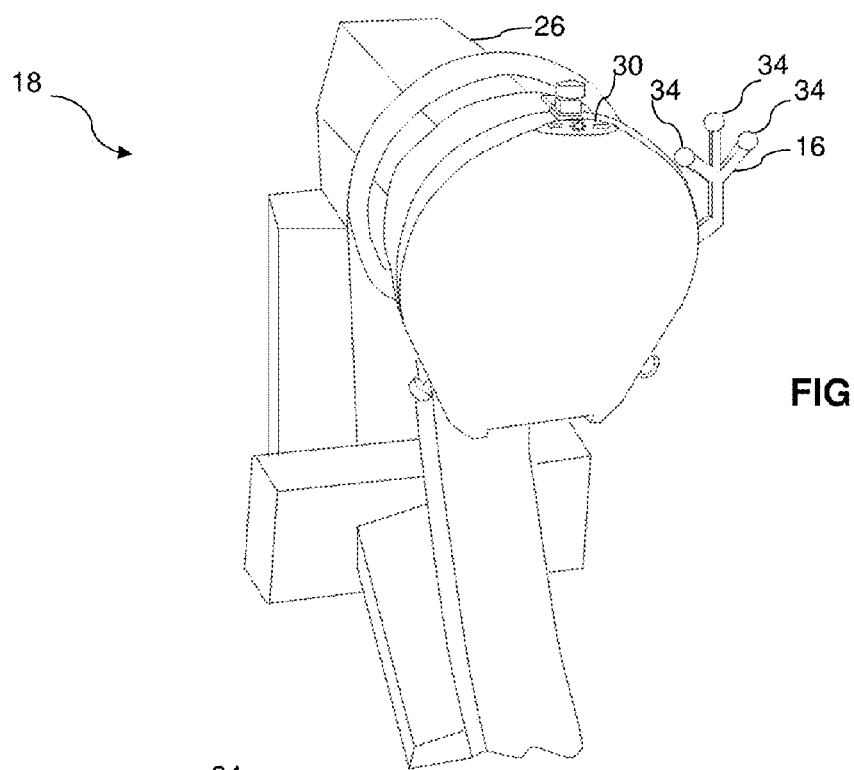
FIG. 2 is a perspective view of a C-arm fluoroscope comprising part of the system of FIG. 1.

The intraoperative imaging system 18 may be any commercially available C-arm fluoroscope 26 communicatively linked to a C-arm display 28 with an IR-reflective tracking array 16 attached, for example, to the signal receiver. As illustrated in FIG. 2, the IR-reflective tracking array 16 is preferably attached to the C-arm 26 by one or more mating points (not shown) on a reticle 30. By way of example, reticle 30 may be the reticle shown and described in PCT Patent App. No. PCT/US2008/012121, entitled "Surgical Trajectory Monitoring System and Related Methods," and filed on Oct. 24, 2008, the entire contents of which is hereby incorporated by reference as if set forth fully herein.

Figure 3:
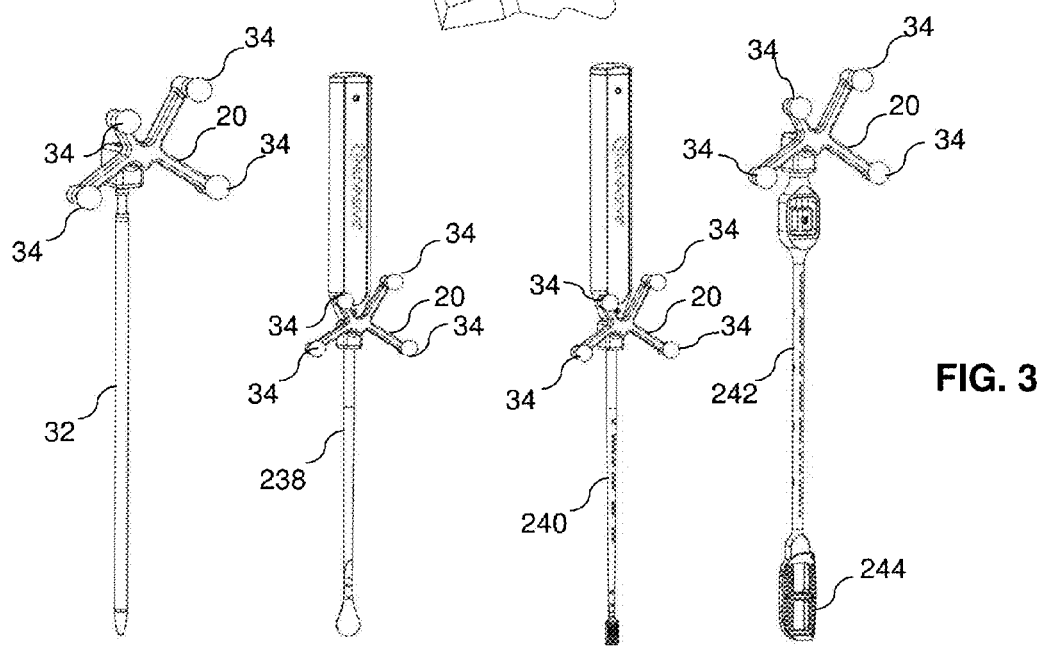
FIG. 3 is a perspective view of various surgical objects that may be tracked with the system of FIG. 1.

As depicted in FIG. 3, the surgical objects to be tracked may be one or more surgical instruments including initial dilator 32, cobb 238, rasp 240, and intervertebral implants 244 (shown in FIG. 3 attached to an implant inserter 242). Though not shown, and by way of example only, other surgical objects to be tracked may include retractor blades and intervertebral implant trials, among others. Indeed any instrument, implant, or device suitable for use in spine surgery may be outfitted with an IR-reflective tracking array 20 and tracked within the surgical field in accordance with the present disclosure. FIG. 1 illustrates an IR-reflective tracking array 16 positioned on an intraoperative imaging device 18 and an IR-reflective tracking array 20 positioned on an initial dilator 32. Each IR-reflective tracking array 16, 20 has IR-reflective spheres 34 arranged in a calculated manner somewhere along its length. Spatial position data about a surgical object may be acquired in its raw form relative to the IR position tracking sensor's 14 local coordinate system with each IR-reflective tracking array 16, 20 determining its own coordinate system.

The system 10 further comprises a neuromonitoring system 36 communicatively linked to the position tracking system 12 via the control unit 22. By way of example only, the neuromonitoring system 36 may be the neuromonitoring system shown and described U.S. Pat. No. 8,255,045, entitled "Neurophysiologic Monitoring System" and filed on Apr. 3, 2008, the entire contents of which is hereby incorporated by reference as if set forth fully herein. The neuromonitoring system 36 may be further configured to perform neuromonitoring as a surgical access corridor is created (e.g. a lateral access corridor created via a sequential dilation assembly) and/or maintained (e.g. via a retractor assembly) and as one or more surgical implants are placed into the body (e.g. a pedicle screw). The neuromonitoring system 36 may also be configured to: 1) assess the depth of nearby nerves relative to a surgical object; 2) localize the relative position of the nerves once the surgical object reaches the spinal target site (e.g. a lateral aspect of the spine); 3) couple the neurophysiology data with the previously-acquired positional data of the surgical object; and 4) present the combined data to the user via a virtual fluoroscopic image.

Details of the surgical tracking system 10 are discussed in conjunction with a first exemplary use thereof for monitoring a minimally-invasive, lateral trans-psoas approach to the spine during a lateral lumbar interbody fusion. By way of example, the system 10 may be used for monitoring the approach during a lateral trans-psoas procedure shown and described in U.S. Pat. No. 7,905,840, entitled "Surgical Access System and Related Methods," and filed on Oct. 18, 2004, the entire contents of which is hereby incorporated by reference as if set forth fully herein.

Figure 4:
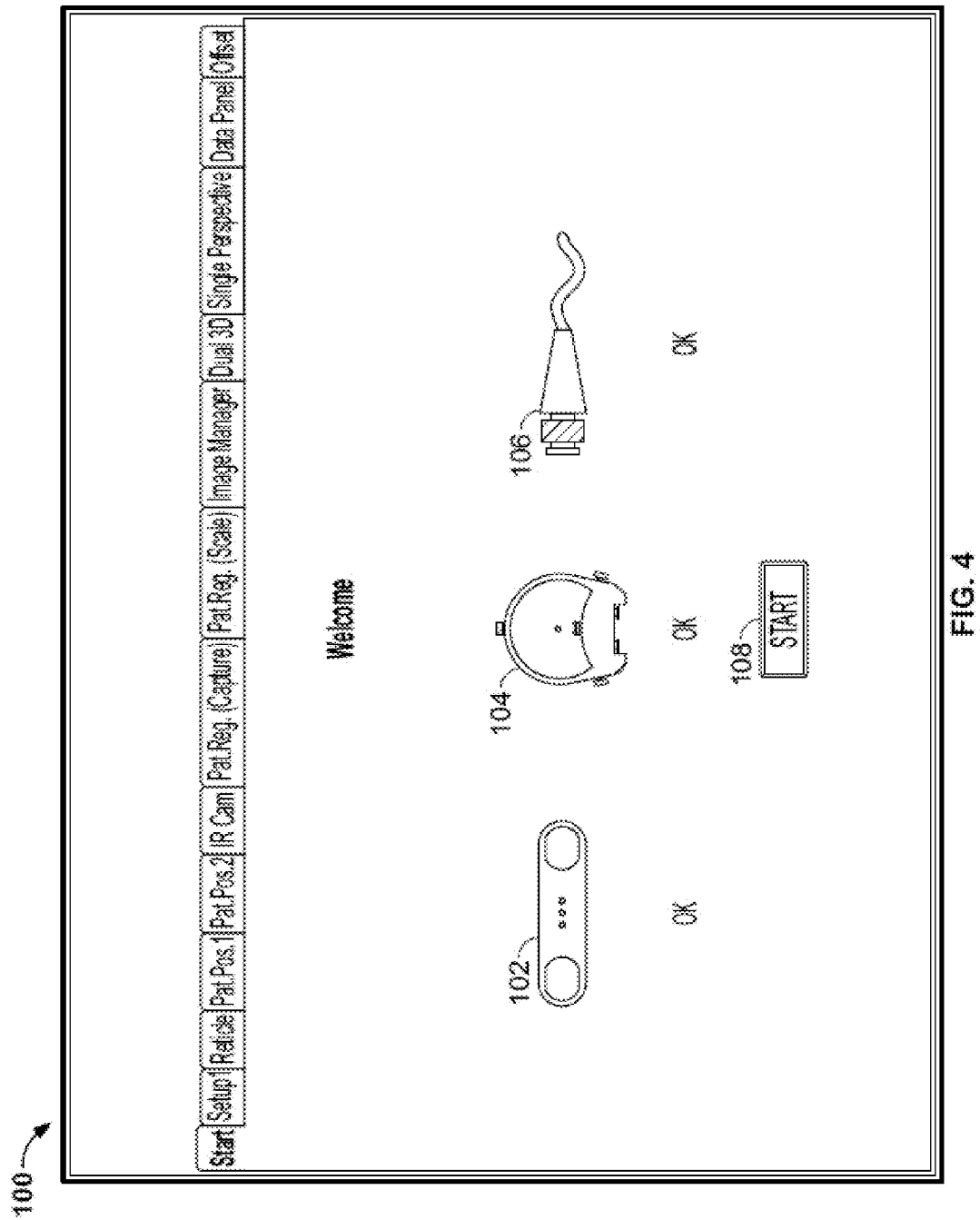
FIG. 4 is a screen shot depicting an example welcome screen of the system of FIG. 1.

FIGS. 4-26 illustrate, by way of example only, one embodiment of a screen display 100 of the control unit 22 capable of receiving input from a user in addition to communicating feedback information to the user. In this example (though it is not a necessity), a graphical user interface (GUI) is utilized to enter data directly from the screen display 100. FIG. 4 depicts a welcome screen in accordance with one exemplary embodiment. The system 10 is configured to detect the connection status of each of its required components. By way of example only, icons 102, 104, 106 indicate the connection status of the IR position sensor 14, C-arm reticle 30, and C-arm video output, respectively. If one or more required components are not connected or are connected improperly, the display 100 may alert the user to address the issue before proceeding via textual, audio, and/or visual means (e.g., textual messages, audible tones, colored screen, blinking screen, etc.). A separate indicator may alert the user once all of the required components are properly connected. For example, an "OK" message below each of icons 102, 104, and 106 indicates all components are properly connected. Selecting the "Start" button 108 proceeds to the next screen.

Figure 5:
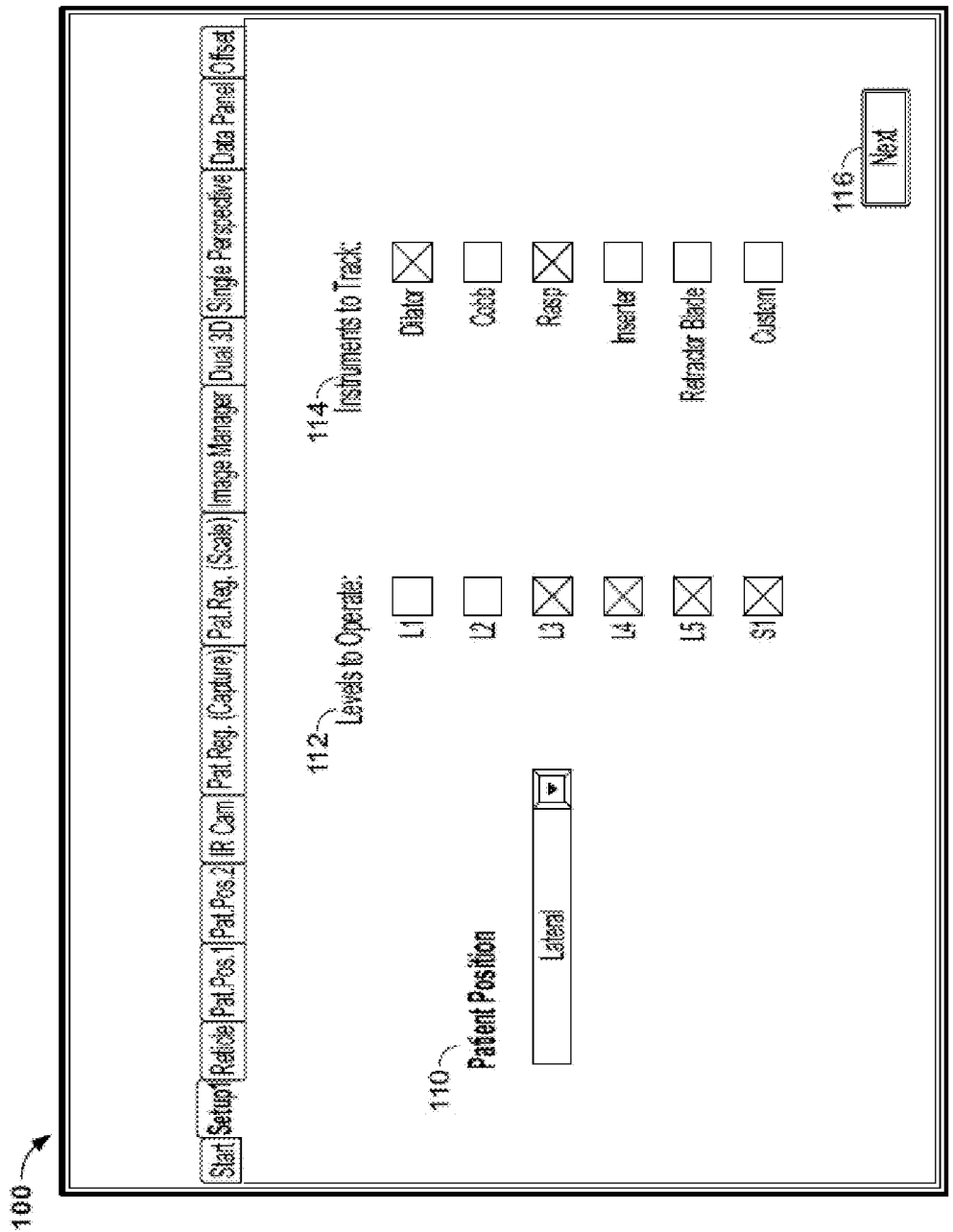
FIG. 5 is a screen shot depicting an example procedure information screen of the system of FIG. 1.

FIG. 5 illustrates an example procedure input screen. The user may use the screen 100 to input information into one or more selection fields regarding the patient and procedure. The selection fields may be drop-down menus or checkboxes pertaining to patient positioning 110 (e.g., lateral, prone), spinal levels to be operated on 112 (e.g., L1, L2, L3, L4, L5, S1), and surgical instruments to track 114 (e.g., dilator, cobb, rasp, inserter, retractor blade, custom/other). Once the user has provided the requested information, selecting the "Next" button 116 proceeds to the next screen.

The tracked surgical objects are preferably monitored with respect to the position of, and displayed onto the anatomy of one or more virtual fluoroscopic images from the perspective of, the intraoperative imaging system 18 (not with respect to the position of, and the perspective of, the IR position sensor 14). Thus a surgical object is referenced off of the location of the C-arm 26 and its positional information is determined relative to coordinate system of the tracking array 16 of the c-arm 26 (the "working coordinate system").

To track objects with respect to the C-arm 26, the coordinate system of the IR reflective tracking array 16 affixed to the C-arm 24 is oriented in the direction of the x-ray beam according to a preferred embodiment. By way of example, one of the axes of the IR reflective tracking array's 16 coordinate system is preferably oriented parallel to the beam axis, and the definition of this orientation is known in the position tracking software resident on the control unit 22. Prior to installing the reticle 30, the C-arm 26 is placed in the traditional lateral position (with the arc of the "C" pointing straight down (0°) and the axis representing the x-ray beam at 90°). Accelerometers (not shown) installed inside the reticle 30 may be used to generate angular data such that the reticle 30 can be installed at the 12 o'clock position relative to the surface of the C-arm signal receiver. After properly installing the reticle 30, the C-arm 26 can be placed in a traditional anterior/posterior (A/P) position. Preferably, the user moves the C-arm 26 to this position with the aid of the accelerometer readout of the reticle 30 as described in the '121 application. An exact A/P position is achieved when accelerometer's x and y axes both read 0°. This will also verify that the axis of gravity (and the axis of the X-ray beam) is normal to the surface of the C-arm receiver, which corresponds to the plane of the fluoroscopic image. Once this position is verified, the software establishes the corresponding array 16 position as 0°/0° and that the axis of the x-ray beam is parallel to the desired "working coordinate system's" y axis. The system 10 may then report to the user when the beam/image axis is at 90° or the "true" lateral position.

Figure 6:
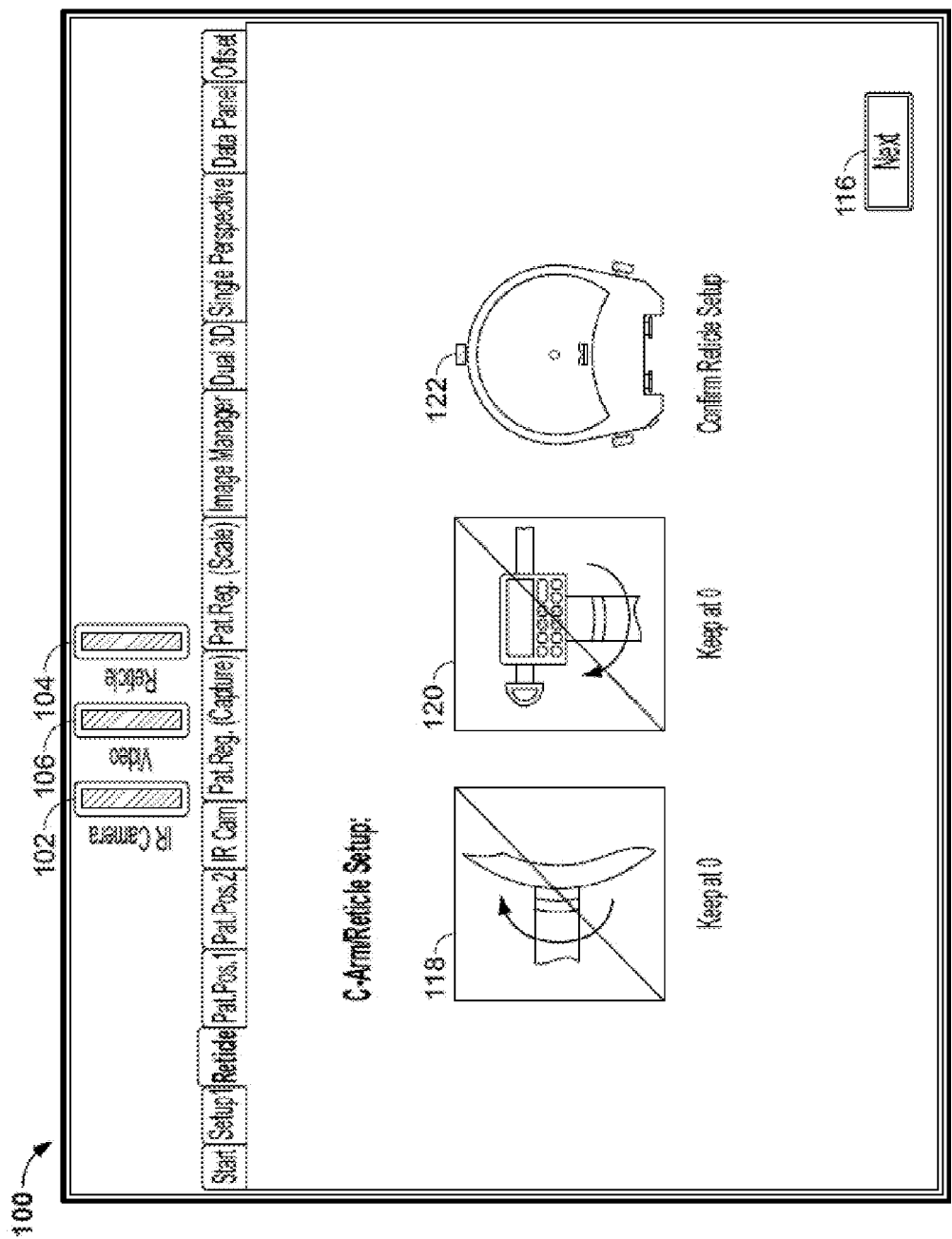
FIG. 6 is a screen shot depicting an example C-arm setup screen of the system of FIG. 1.

An exemplary C-arm setup and instruction screen is illustrated in FIG. 6. To assist the user in setting up the working coordinate system of the C-arm 26, the screen 100 may provide helpful instructions for the user for setting up the C-arm 26 and reticle 30 via, by way of example only, instruction fields 118, 120, and 122. Once the user has acknowledged the movement restrictions and confirmed the proper reticle 30 setup, selecting the "Next" button 116 advances to the next screen.

Figure 7:
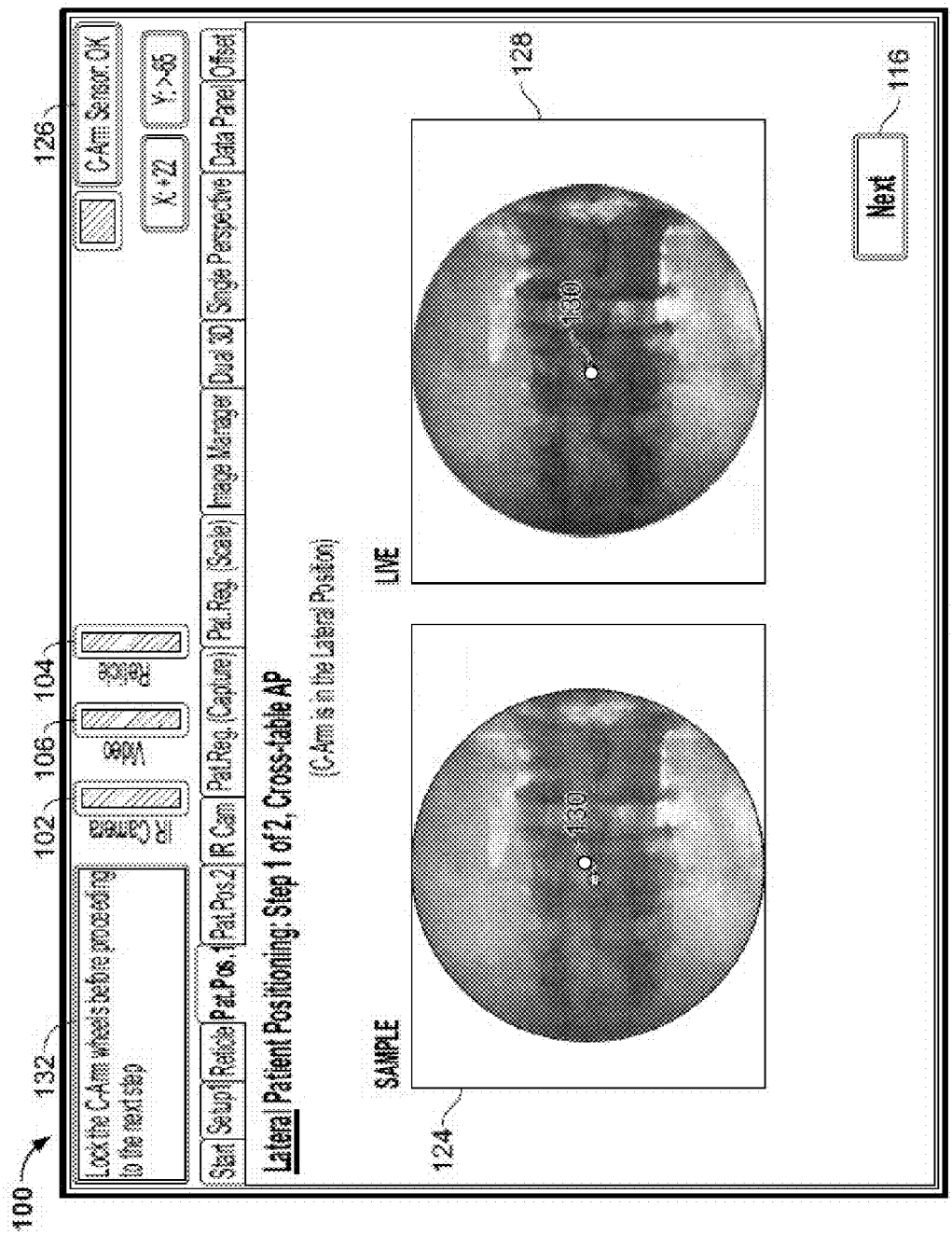
FIG. 7 is a screen shot depicting an example patient positioning screen during a first step of a patient positioning sequence.
Figure 8:
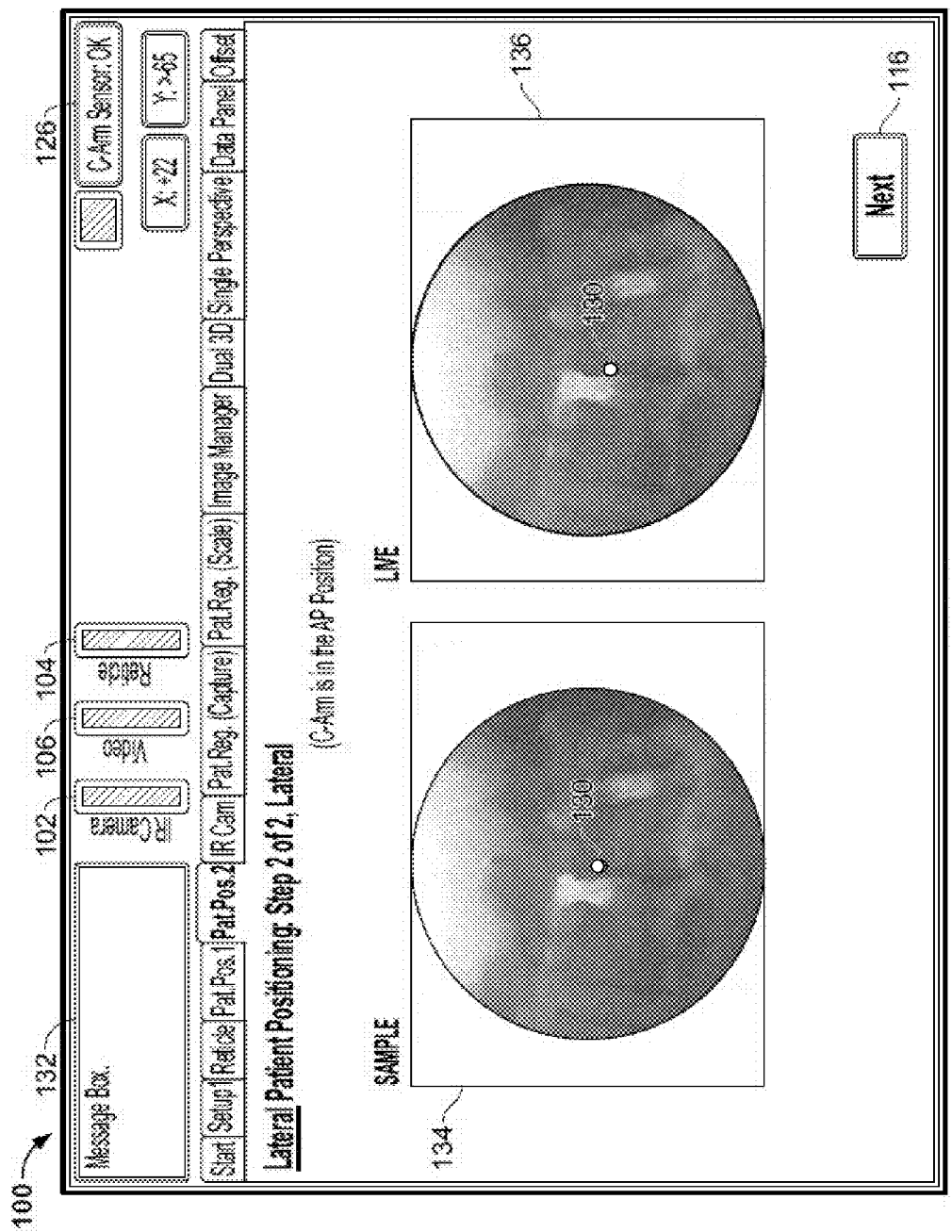
FIG. 8 is a screen shot depicting the example patient positioning screen during a second step of the patient positioning sequence.

Following setup, the user should ensure that the patient is properly positioned. FIGS. 7 and 8 depict exemplary display screens 100 that may assist the user with patient positioning.

A first step to confirming patient positioning is to obtain a cross-table A/P fluoroscopic image of the patient in the lateral decubitus position. The screen display 100 may show the user an ideal (sample) cross-table AP image 124 and a C-arm status indicator field 126 to ensure that the C-arm 26 is in the true lateral position. A cross-table A/P image 128 is taken (and re-taken as needed) to approximately match the sample cross-table A/P image 124. A virtual center dot 130 is superimposed on both cross-table A/P images 124, 128. Once image 128 matches sample 124, the user may be provided with one or more additional instructions via message box 132. For example, the message box 132 may remind the user to lock the C-arm wheels before proceeding to the next step. Selecting the "Next" button 116 advances the screen display 100 to the next screen.

A second step to confirming patient positioning is to obtain a patient-lateral fluoroscopic image of the patient in the lateral decubitus position. The screen display 100 may show the user an ideal (sample) lateral image 134 and a C-arm status indicator field 126 to ensure that the C-arm is positioned 90° from the previous cross-table position. A lateral image 136 is taken (and retaken as needed) to approximately match the sample lateral image 134. A virtual center dot 138 is superimposed on both lateral images 134, 136. When the user is finished confirming this view, the "Next" button 116 is selected to advance the display screen 100 to the next screen.

Figure 9:
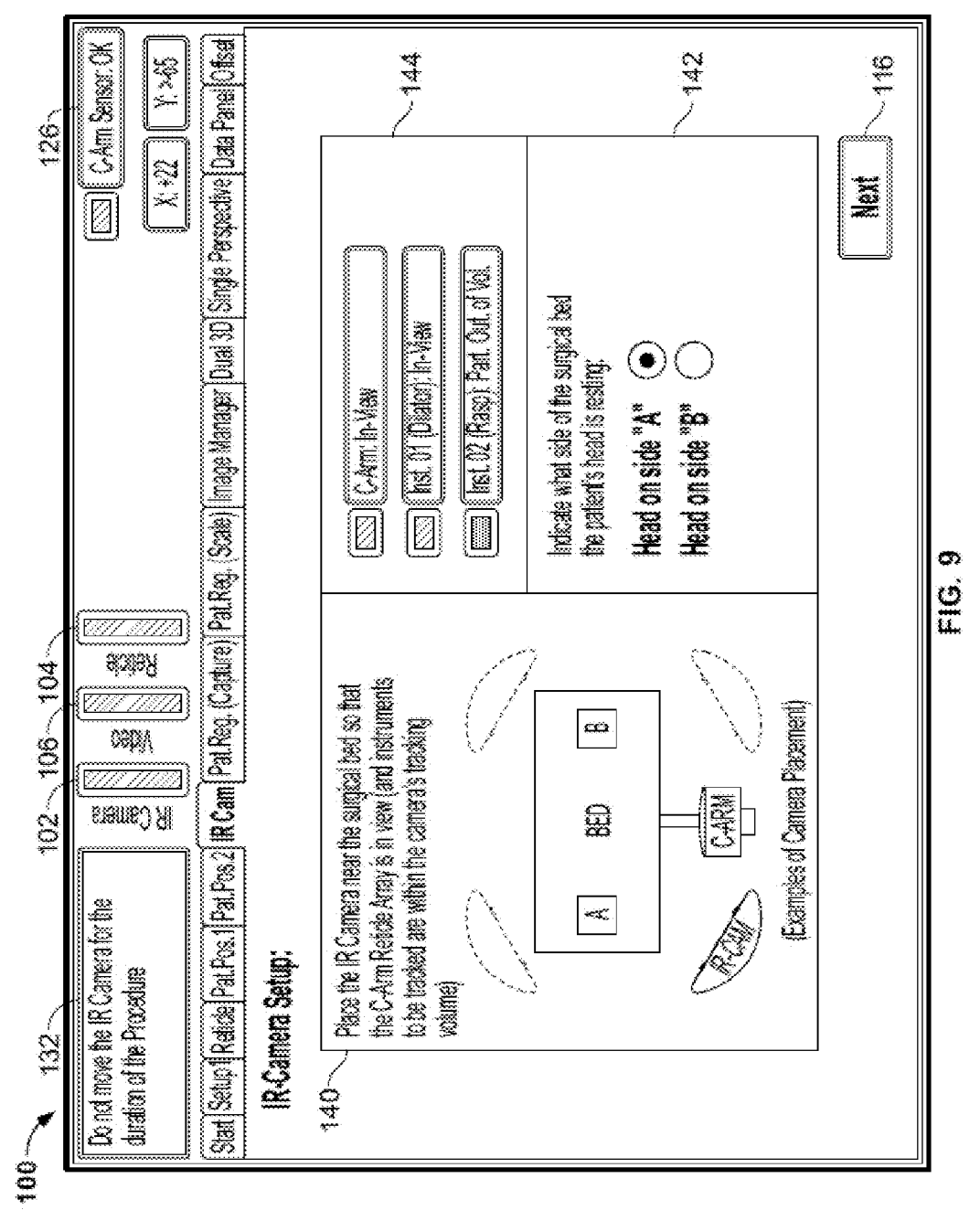

After patient positioning is complete, the IR position sensor 14 can be positioned near the surgical field. The IR position sensor 14 should be positioned so that the C-arm array 16 can be tracked in both the A/P and lateral positions. Also, the instrument tracking array 20 should be visible within the tracking volume of the IR position sensor 14. FIG. 9 illustrates an exemplary IR position sensor position field screen. The display screen 100 may present the user with an exemplary configuration setup and instructions (shown by way of example only in instruction panel 140). Instruction panel 140 instructs the user to position the IR position sensor 14 near the surgical bed so that the IR reflective tracking array 16 on the C-arm 26 is in view of the IR position sensor 14 and the surgical objects to be tracked within the IR position sensor's 14 tracking volume. The user may also input information regarding the general positioning of the patient relative to the IR position sensor 14 in positioning input field 142. By way of example only, the user may be instructed to select which side of the surgical bed the patient's head is resting on (e.g., side "A" or side "B"). After the general position of the IR position sensor 14 has been inputted, the system 10 may evaluate whether the position of the IR position sensor 14 relative to the IR reflective tracking arrays 16, 20 is optimal for data acquisition. According to some implementations, the system 10 may provide instructions as to where to move the IR position sensor 14 to achieve optimal placement in message box 132 (e.g., towards the patient, away from the patient, towards the feet, towards the head). According to some implementations, the display screen 100 may present the status of one or more tracked objects via tracked object status field 144. It is to be appreciated that any visual indicator (textual, graphic, color) may be used to indicate status of the tracked object or objects relative to the IR position sensor 14. As shown by way of example in FIG. 9, the tracked object status field 144 shows three surgical instruments being tracked: the C-arm, the initial dilator, and the rasp. The tracked object status field 144 also indicates (via text and/or color indicators) that the C-arm and the initial dilator are within view of the IR position sensor 14 but that the rasp is not. Should the user wish to use the rasp, it will be necessary to move it within the tracking volume of the IR position sensor 14. Once the optimum IR position sensor 14 placement has been achieved, the user may then select the next button to continue to the patient registration protocol. Again, various reminders may be provided to the user via message box 132 (e.g., the user may be reminded not to move the IR position sensor for the remainder of the procedure).

Figure 10:
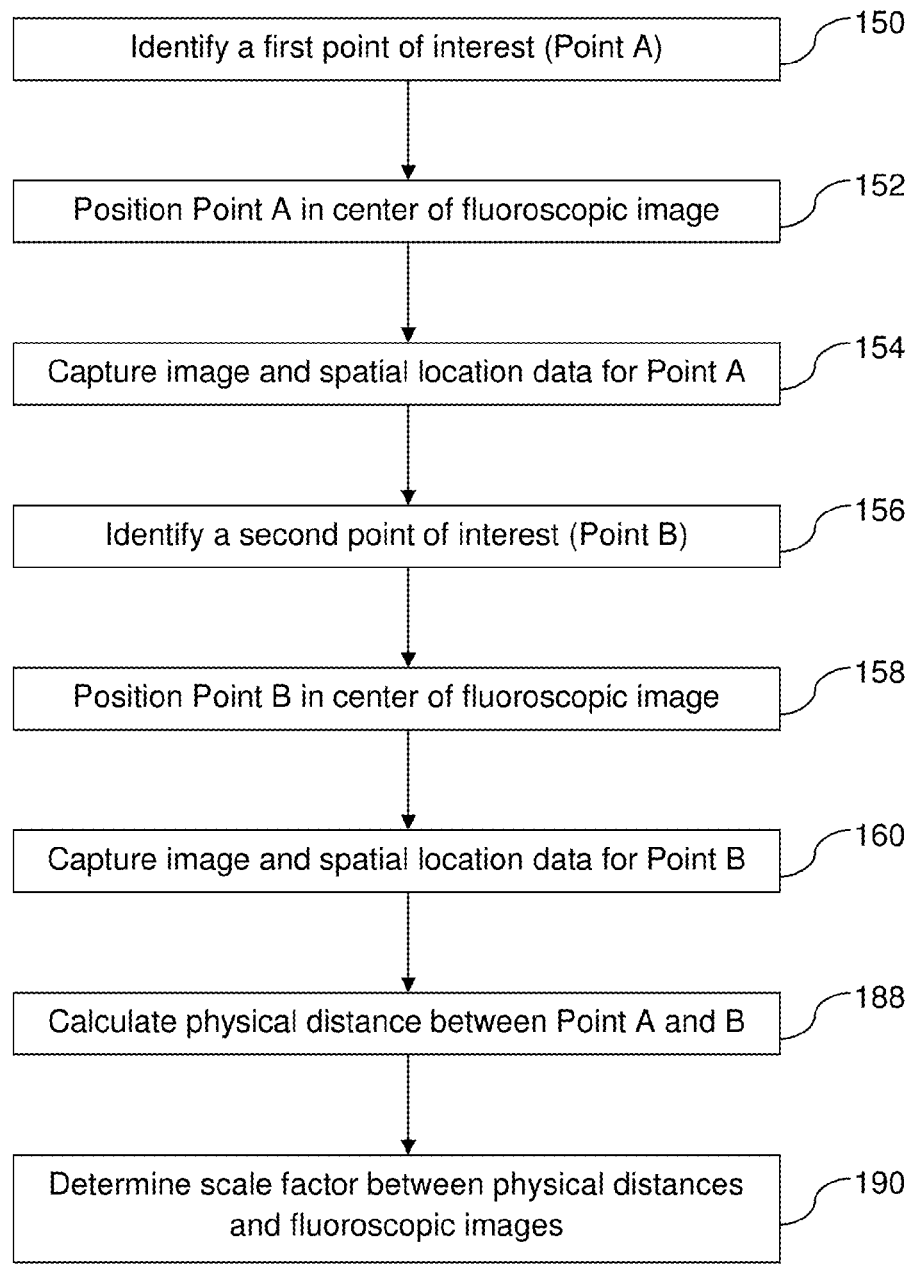
FIG. 10 a flow chart indicating the steps of a patient registration and scaling sequence of the system of FIG. 1, according to one example embodiment.

With the C-arm 26, patient, and IR position sensor 14 properly positioned, a user may proceed to the registration and scaling process. In some implementations, the patient registration portion of the process involves defining two or more points of interest for each fluoroscopy view. FIG. 10 depicts a flowchart of the patient registration process for a given view. First, the user identifies a first point of interest (Point A) at Step 150. Next, the user positions the C-arm 26 such that Point A is in the center of the fluoroscopic image at Step 152 using a virtual center marker as will be described in greater detail below. Once the user indicates that this point is satisfactory, the position tracking software captures the current image, the x, y, z position of the reticle 30, and the rotational position of the reticle 30 with respect to Point A at Step 154. At Step 156, the user identifies a second point of interest (Point B). It is to be appreciated that the user may choose any part of the anatomy for Point B that is not Point A. Next, the user positions the C-arm 26 such that Point B is in the center of the fluoroscopic image at Step 158. Once the user indicates that this point is satisfactory, the position tracking software captures the current image, the x, y, and z positions of the reticle 30, and the rotational position of the reticle 30 with respect to Point B at Step 164. In some implementations, points of interest may be acquired in two or more views (e.g. lateral and A/P views). The steps described above are repeated for each view and once all desired views are registered, the images for each view (i.e. the A/P view's scale and/or the lateral view's scale) may be scaled.

Scaling may be accomplished in a number of ways (e.g., manually or automatically). In some automatic implementations, the system 10 lines up the images to create the best anatomy match via image recognition. In manual implementations, this may be done, by way of example, by presenting a user with a scaling image and a backdrop image and prompting the user to define where one or more points are located on a backdrop image (as will be described in further detail below). The system 10 measures the physical distance between Point A and Point B (Step 188) and determines a scale factor by correlating the physical distance between Points A and B with the number of pixels between Points A and B on the display 24 (Step 190). This "scale" factor may then be used to calculate the movements of the 3D-generated virtual instruments and implants against the 2D x-ray image in that particular view, among other things. With both of the A/P and lateral views registered and scaled, the surgical volume is defined for the system and the C-arm 26 may then be articulated to a primary position (e.g., a lateral position). The C-arm 26, in this position, acts as the reference object for all other objects being tracked. Effectively, the other tracked objects (i.e. instrumentation, implants, etc.) will be referenced from the C-Arm array's 16 local coordinate system, thereby allowing the movements of the 3D-generated instruments and implants against the 2D image in each view.

The screen display 100 (explained, for illustrative purposes, with reference to FIG. 11) may include various features for assisting the user with the patient registration and scaling process. Screen display 100 may include an image acquisition panel 162, a patient registration task panel 164, and an instruction panel 166. By way of example only, the image acquisition panel 162 preferably includes the live fluoroscopic image that is inputted into the system 10 from the intraoperative imaging system 18 via a C-arm input cable. This fluoroscopic image may be the image that the user selects to be the anatomical lateral backdrop (i.e. the virtual lateral fluoroscopic image). By way of further example, the patient registration task panel 166 may include a list of the registration steps completed and those yet to be completed and the instruction panel 166 may include specific directions to the user for what actions to perform to complete the first step in the acquisition process. The screen display 100 may also include a plurality of buttons for navigating through the patient registration process. For example, selecting the "Capture" button 168 obtains the position and image information for the first lateral fluoroscopy shot, selecting the "Reset" button 170 restarts the patient registration process, selecting the "Back" button allows the user to see what was captured for a previously-acquired image, and selecting the "Next" button 174 advances to the next step in the patient registration process.

Figure 11:
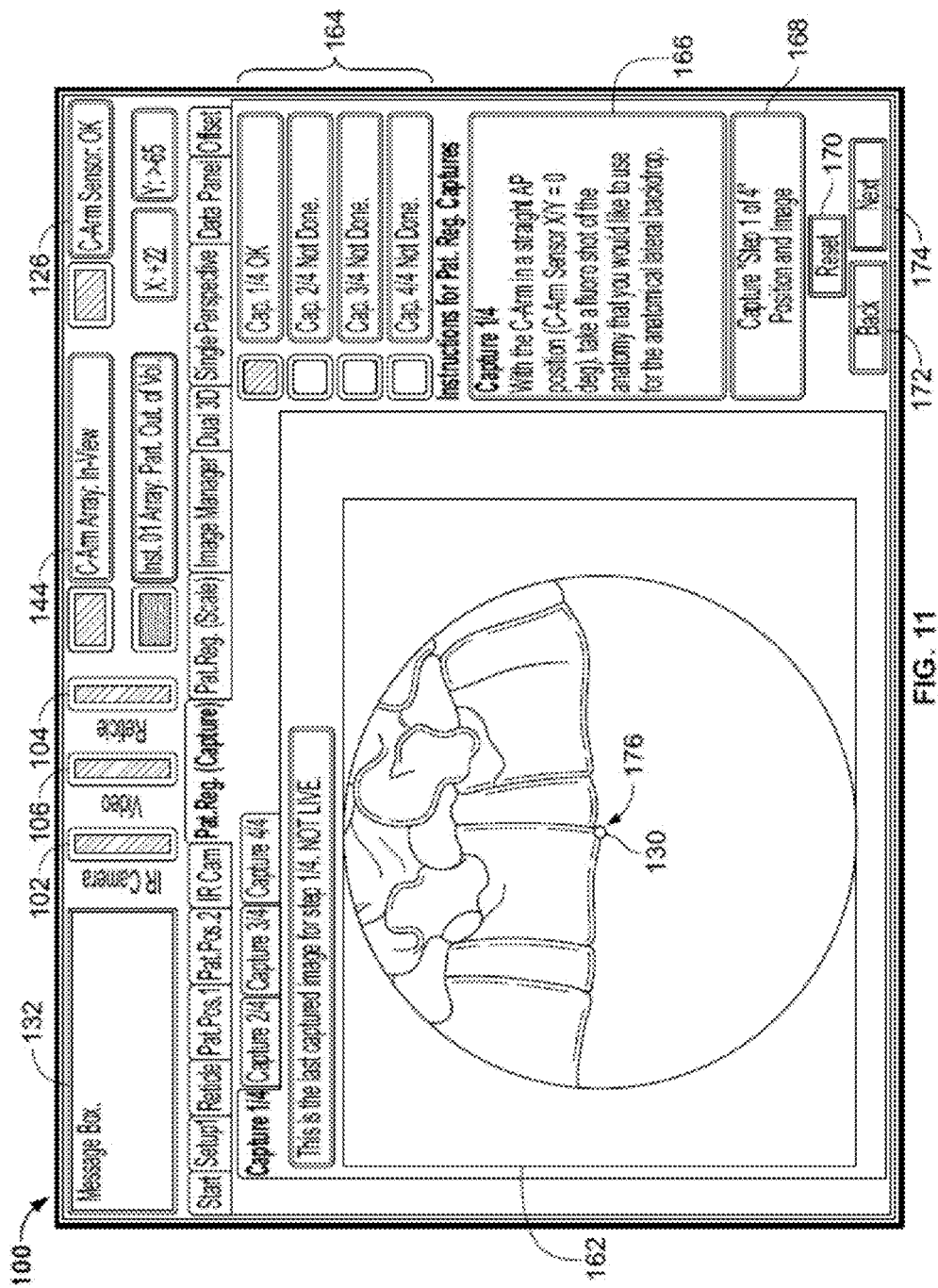
FIG. 11 is a screen shot depicting an example registration and scaling screen during a first step in the example patient registration sequence of FIG. 10.

FIGS. 11-14 depict the screen display 100 during the steps of the patient registration process according to one exemplary embodiment. As shown in FIG. 11, Point A 176 is defined in the anatomical lateral view of the patient with the C-arm 26 in the A/P position. By way of example only, the chosen anatomy for Point A 176 is the anterior border of the disc space at the superior vertebra. An image is taken with Point A 176 in the center of the fluoroscopic image as shown in image acquisition panel 162. Once the user indicates that this point is satisfactory by selecting the "Capture" button 168, the software captures the following data points: 1) the current image and 2) the x, y, z, and rotational position of the reticle 30 with respect to Point A 176. This lateral image will be used for the "virtual" patient-lateral 3D backdrop 178. Once the fluoroscopic image has been taken and the positional data captured, the user can select the "Next" button 174 to proceed to the next registration step.

Figure 12:
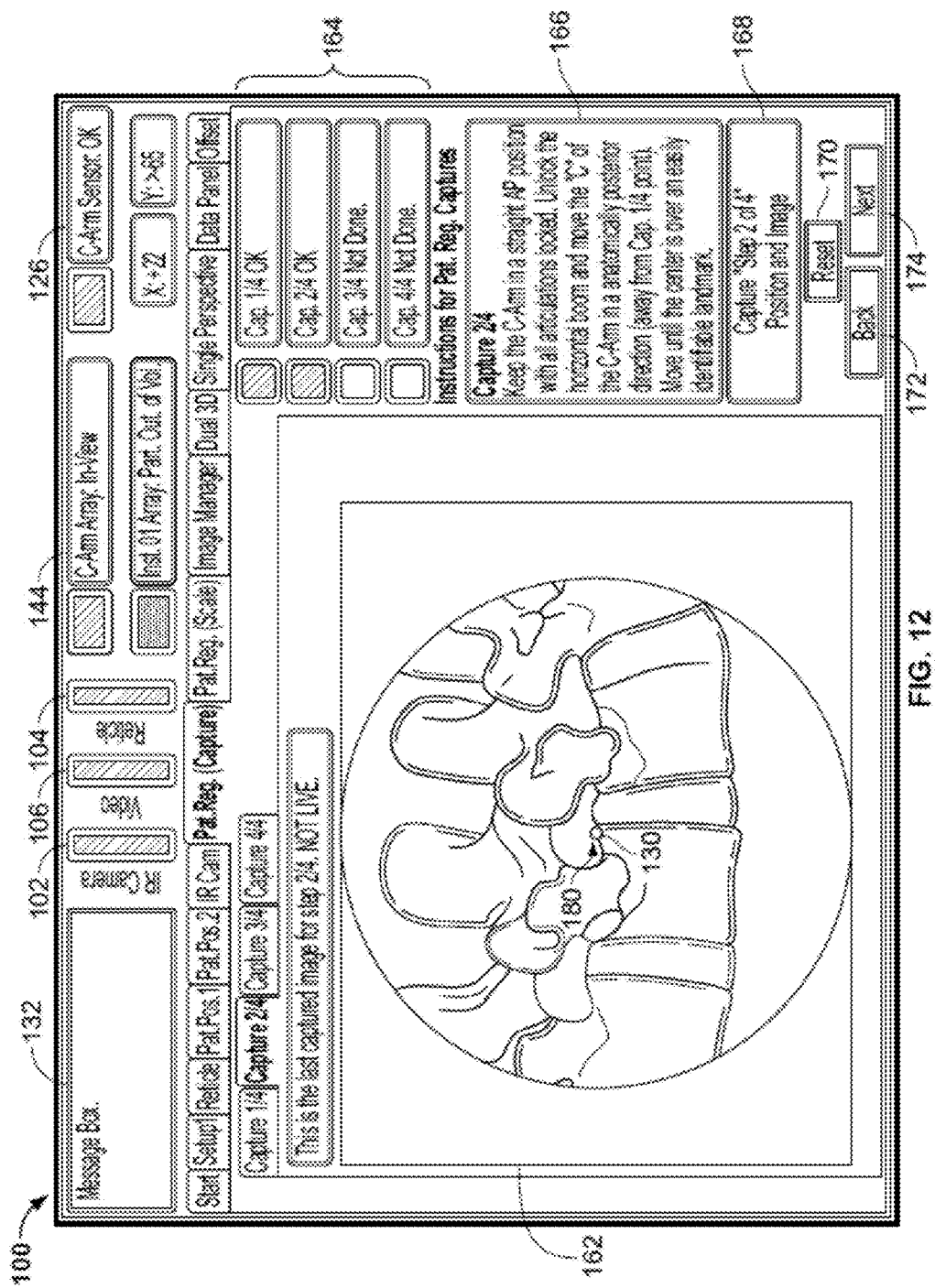
FIG. 12 is a screen shot depicting the example registration and scaling screen during a second step in the example patient registration sequence of FIG. 10.

As shown in FIG. 12, Point B 180 is then defined in the anatomical lateral view of the patient with the C-arm 26 in the A/P position. It is to be appreciated that the user may choose any part of the anatomy for Point B 180 that is not Point A 176. Preferably, Point B 180 is any point on the anatomy that is either anterior or posterior to Point A 176. For convenience, this movement from Point A 176 to Point B 180 is constrained to one axis (i.e., the line formed between Point A 176 and Point B 180 is parallel to the anterior-posterior axis). By way of example only, the chosen anatomy for Point B 180 is the posterior border of the disc space at the superior vertebrae. As shown in instruction panel 166, the system 10 may provide the user with instructions for taking the second image. An image is then taken with Point B 180 in the center of the fluoroscopic image as shown in image acquisition panel 162. Once the user indicates that Point B 180 is satisfactory by selecting the "Capture" button 168, the software captures the following data points: 1) the current image and 2) the x, y, z, and rotational position of the reticle 30 with respect to Point B 180. Once the image has been taken and the positional data captured, the user can select the "Next" button 174 to proceed to the next registration step.

Figure 13:
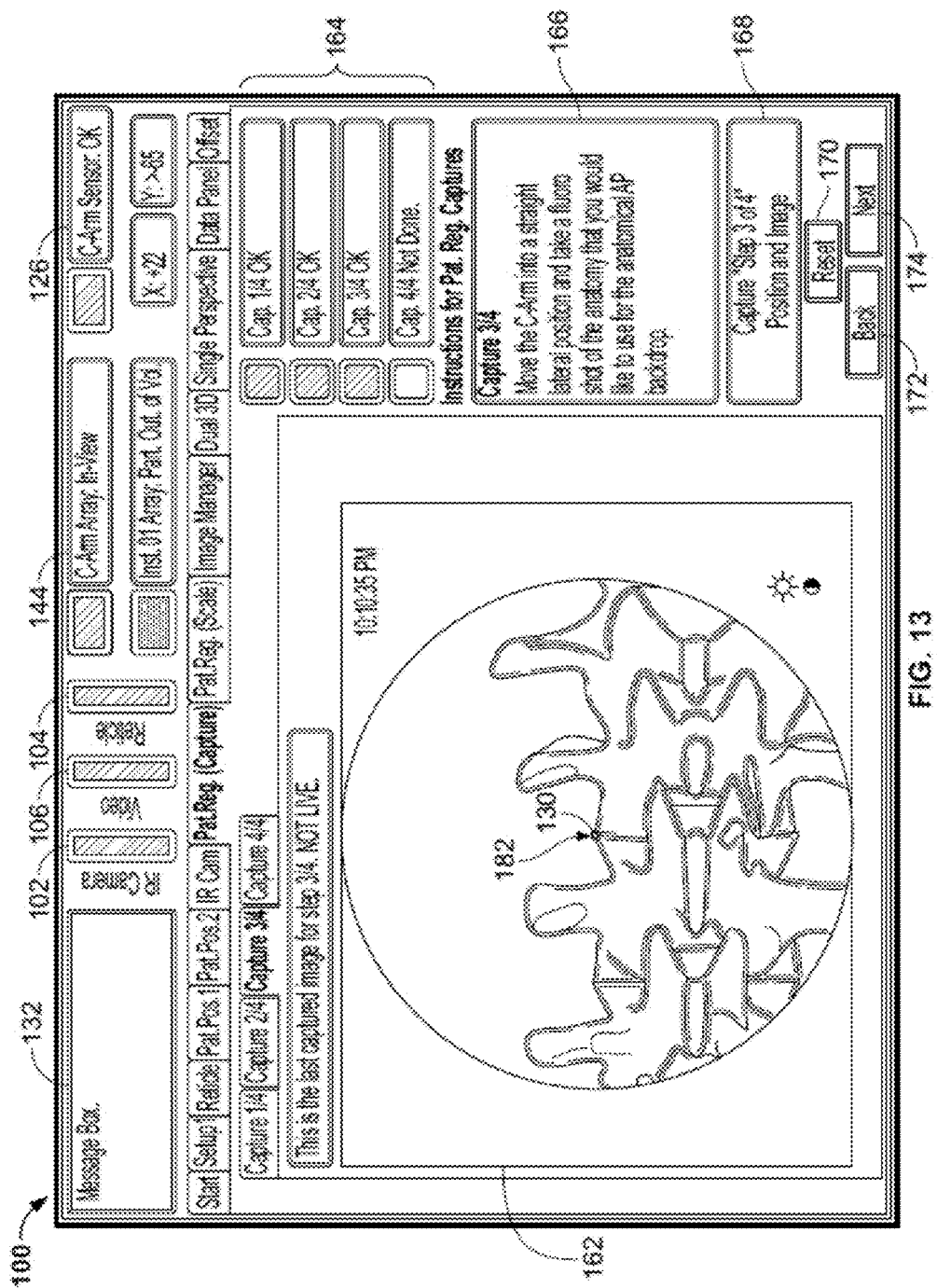
FIG. 13 is a screen shot depicting the example registration and scaling screen during a third step in the example patient registration sequence of FIG. 10.

As shown in FIG. 13, Point A' 182 is then defined in the anatomical A/P view of the patient with the C-arm 26 in the lateral position. By way of example only, the chosen anatomy for Point A' 182 is the ipsilateral border of the disc space. An image is taken with Point A' 182 in the center of the fluoroscopic image as shown in image acquisition panel 162. Once the user indicates that this point is satisfactory by selecting the "Capture" button 168, the software captures the following data points: 1) the current x-ray image and 2) the x, y, z, and rotational position of the reticle 30 with respect to Point A' 182. This A/P image will be used for the patient-lateral 3D backdrop 184 (i.e., the virtual A/P fluoroscopic image). Once the image has been taken and the positional data captured, the user can select the "Next" button 174 to proceed to the next registration step.

Figure 14:
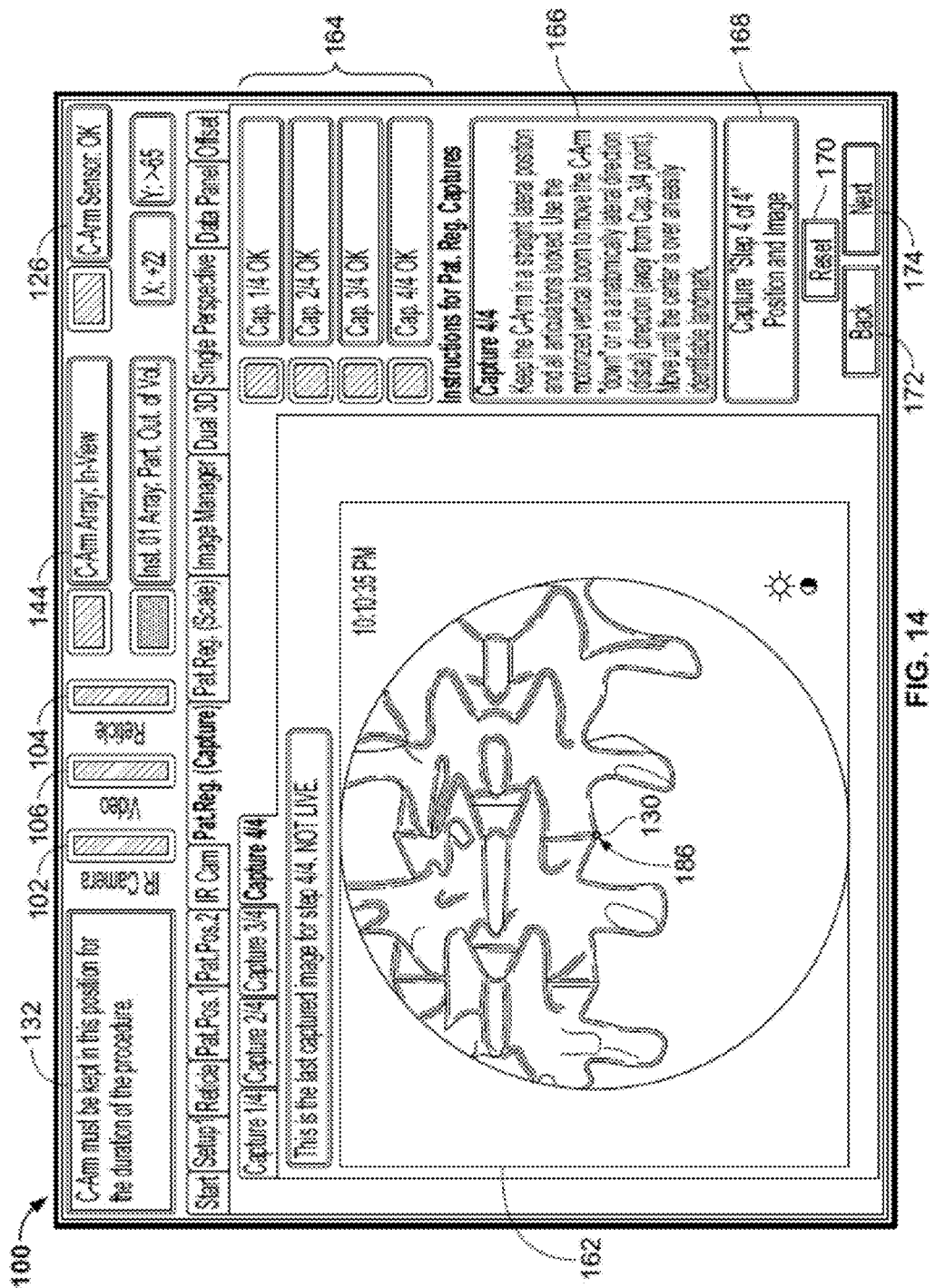
FIG. 14 is a screen shot depicting the example registration and scaling screen during a fourth step in the example patient registration sequence of FIG. 10.

As shown in FIG. 14, Point B' 186 is then defined in the anatomical A/P view of the patient with the C-arm 26 in the lateral position. By way of example only, the chosen anatomy for Point B' 186 is the contralateral border of the disc space. An image is taken with Point B' 186 in the center of the fluoroscopic image as shown in image acquisition panel 162. Once the user indicates that Point B' 186 is satisfactory by selecting the "Capture" button 168, the software captures the following data points: 1) the current image and 2) the x, y, z, and rotational position of the reticle 30 with respect to Point B' 186. Once the image has been taken and the positional data captured, the user can select the "Next" button 174 to complete the patient registration process. In some implementations, the user may be advised via message box 132 or a pop-up window that the C-arm 26 must be kept in this last registration position for the duration of the surgical procedure. In other implementations, the user may choose between the first, second, and merged image in both the A/P and lateral views for display. In yet other implementations, the image may be manipulated to orient the image according to user preference.

Figure 15:
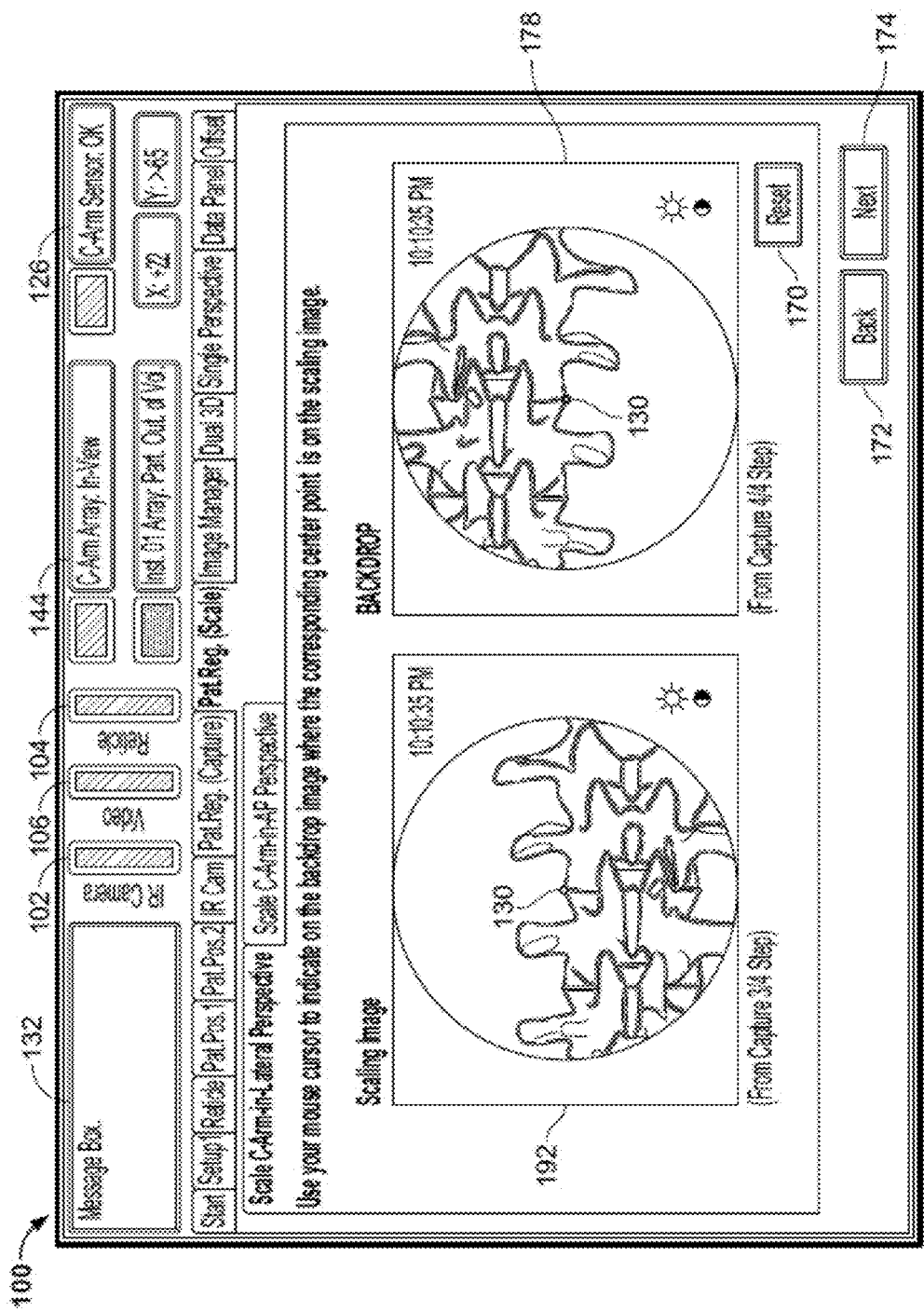
FIG. 15 is a screen shot depicting the example registration and scaling screen during a first step in the example scaling sequence of FIG. 10.
Figure 16:
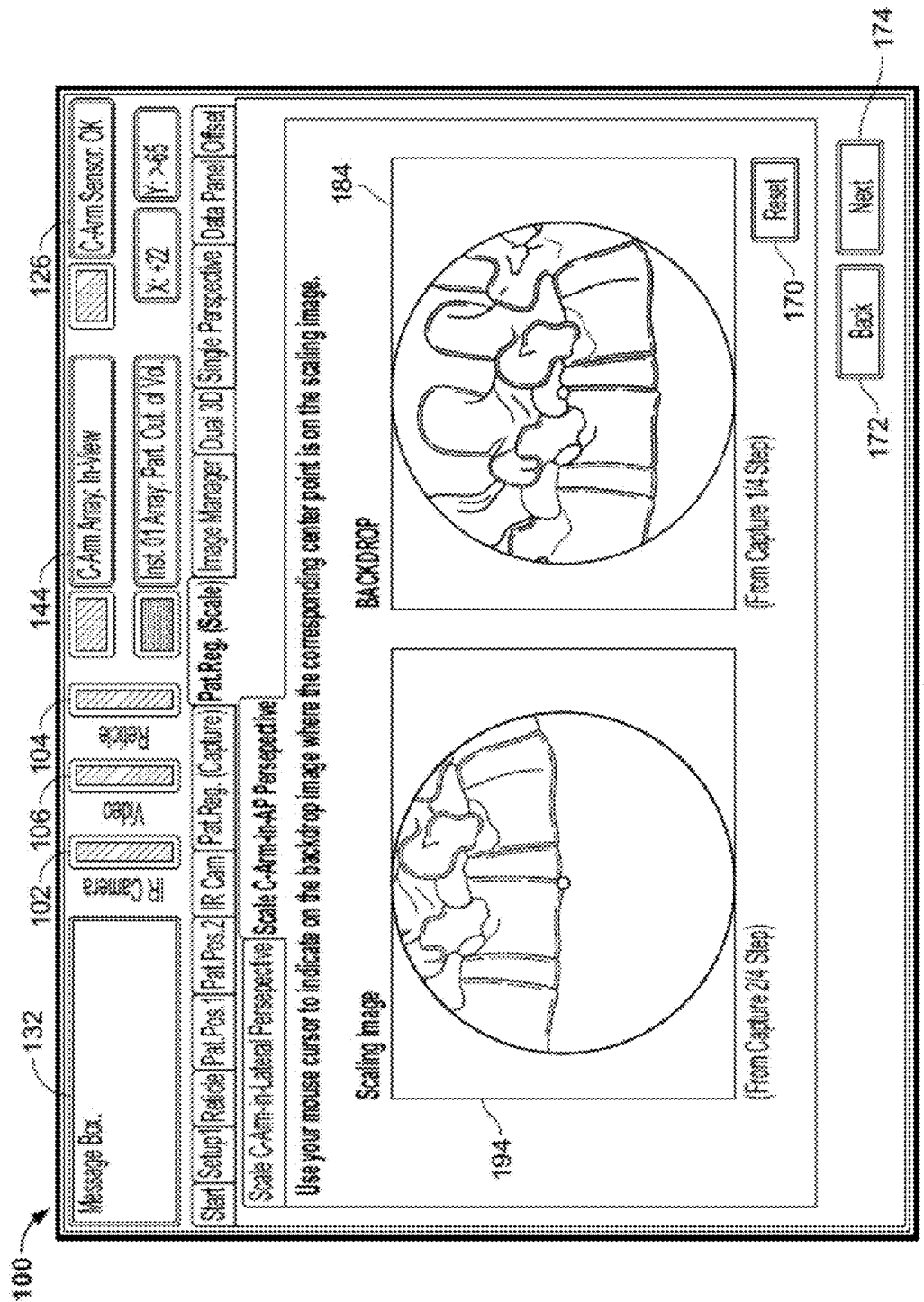
FIG. 16 is a screen shot depicting the example registration and scaling screen during a second step in the example scaling sequence of FIG. 10.

As shown in FIG. 15, Point A 176 and Point B 180 are then chosen and entered into the software and the physical distance between Point A 176 and Point B 180 is calculated. Next, the user specifies where Point B 180 is located on backdrop image 178. By way of example only, this can be done manually (as shown in FIG. 15) by presenting the user with the backdrop image 178 alongside the scaling image 192 and prompting the user to define where Point B 180 is on the backdrop image 178 (e.g., using a touch-screen or a mouse). Next, as shown in FIG. 16, Point A' 182 and Point B' 186 are then chosen and entered into the software and the physical distance between Point A' 182 and Point B' 186 is calculated. Next, the user specifies where Point B' 186 is located on backdrop image 184. By way of example only, this can be done manually (as shown in FIG. 16) by presenting the user with the backdrop image 184 alongside the scaling image 194 and prompting to define where Point B' 186 is on the backdrop image 184. These actions allow the software to correlate the physical distance between points with pixel distances between points on the x-ray images. This "scale" factor is used to properly calculate the movements of the 3D generated instrumentation against the 2D x-ray image in the A/P and lateral views, respectively. With both of the A/P and lateral views registered and scaled, the surgical volume is defined for the system 10. Selecting the "Next" button 174 allows the user to proceed to the main tracking screen 200.

Figure 17:
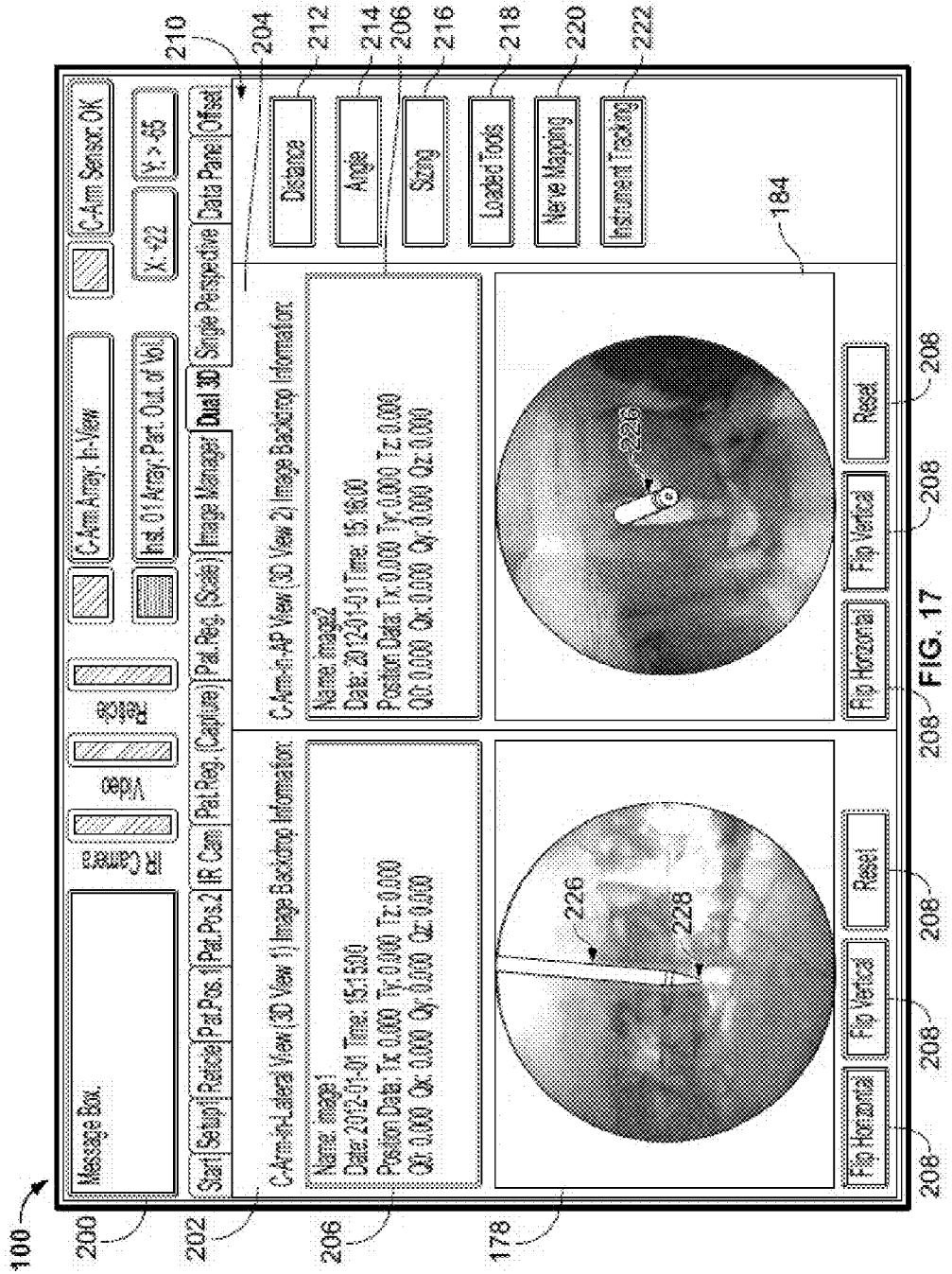
FIG. 17 is a screen shot depicting the system tracking the 3D location of a surgical tool in real time.

According to some implementations, the main tracking screen 200 serves as a starting point for all other available features and functions. FIG. 17 depicts a main tracking screen 200 according to one exemplary embodiment. Main tracking screen 200 includes left tracking panel 202 and right tracking panel 204. Left tracking panel 202 includes backdrop image 178, data box 206, and a plurality of image orientation tabs 208. Right tracking panel 204 includes backdrop image 184, data box 206, and a plurality of image orientation tabs 208. Data box 206 preferably includes the spatial position data acquired regarding the backdrop image 178 or 184. The plurality of image manipulation tabs 208 may be three buttons for reorienting the backdrop image 178 or 184 to suit the user's preference—for example, selecting the "Flip Horizontal" button will invert the backdrop image horizontally, selecting the "Flip Vertical" button will invert the backdrop image vertically, and selecting the "Reset" button will reset the backdrop image 178 or 184 back to its original configuration. As shown by way of illustration in FIG. 17, image 184 is flipped horizontally.

The system 10 may perform various functions that facilitate the surgical procedure depending on the user's preferences or the patient's requirements. The main tracking screen 200 may include numerous features (e.g., represented by tabs 212, 214, 216, 218, and 220 shown within navigation panel 210) for use during the surgical procedure. By way of example only, the system 10 may identify an incision location on the skin, determine the distance from the skin to a desired location within the body, project one or more angles between anatomical points of interest, select the ideal direction for directing or docking a surgical object within the patient, choose the optimal size of implants based on the patient's anatomy, and map neurophysiologic data onto virtual anatomic locations of the patient (each of which will be explained in detail below with reference to a lateral trans-psoas procedure).

Prior to commencing the surgical procedure, the user may wish to verify one or more ideal incision locations. This may be accomplished using the initial dilator 32 with an IR-reflective tracking array 20 attached. To do so, the user selects the "Loaded Tools" tab 218 from the main tracking screen 200. Once the "Loaded Tools" tab 218 is selected, the display screen 100 displays a surgical object menu table of pre-loaded 3D CAD renderings of each instrument and implant available during the procedure in a variety of sizes. The user may use the display 24 to select the surgical object to be tracked (here, an initial dilator 32) and selecting the "Instrument Tracking" tab 222. Next, the user may place the distal tip 224 of the initial dilator 32 laterally over an area of the patient and maneuver it as necessary until a lateral incision location that is substantially lateral to the surgical target site (e.g., the intervertebral disc space) is identified.

The user may also wish to determine the distance between the incision site at the skin to a spinal target site (e.g., the intervertebral disc). The user may select the "Distance" tab 212 from the navigation panel 210 on the main tracking screen 200. The screen 200 will then instruct the user to place the distal tip 224 of the initial dilator 32 on the patient's skin and select a point of interest (e.g. the ipsilateral annulus of the intervertebral disc) and indicate the distance as the distance from the distal tip 228 of the virtual initial dilator 226 to the ipsilateral annulus identified on the virtual fluoroscopic image(s)). This allows the user to know, for example, the length of retractor blades required for a particular patient. This feature has the added benefit of decreasing surgical time because a surgical assistant may assemble the retractor with the correct length of retractor blades while the user-surgeon proceeds with the surgical procedure. It is to be appreciated that the "Distance" function is not limited to the implementation explained above. Indeed, using the "Distance" tab 212, the system 10 can determine the distance from the tip of any actively tracked surgical object to any user-selected location on the virtual fluoroscopic image.

According to other implementations, the screen 200 may instruct the user to select clinically significant boundaries for the surgical procedure on the virtual fluoroscopic images. By way of example, the user may select the lateral borders of the superior and inferior endplates in the A/P view and the anterior and posterior aspects of the vertebral body in the lateral view. The system 10 will provide the user the distance between the x, y, and z coordinates between these locations via the screen 200. Based on these clinical boundaries, the system 10 may also provide the user with an idealized axial view (not shown) of the disc space via an appropriately-scaled 3D rendering of a disc space. Armed with this view, the user may track instruments within the disc space and redirect them as necessary based on this third projected plane.

The user may also wish to determine the angle between two anatomical points on the patient. The user may select the "Angle" tab 214 from the navigation panel 210 on the main tracking screen 200. The screen 200 will instruct the user to place the distal tip 224 of the initial dilator 32 on the patient's skin and select a point of interest on the patient (e.g. the iliac crest at L4-5). Via the screen 200, the system 10 will then project the angle between the virtual initial dilator 226 to the patient's iliac crest at L4-5. This allows the user to know whether the patient's anatomy will accommodate a substantially lateral, retroperitoneal approach to the spine prior to making an incision. This feature has the added benefit of decreasing surgical time and/or preparing for contingency procedures necessitated by challenging anatomy (e.g. a high iliac crest). It is to be appreciated that the Angle function is not limited to the implementation explained above. Indeed, using the "Angle" tab 214, the system 10 can determine the angle between the tip of any actively tracked surgical object to any user-selected location on the virtual fluoroscopic image.

The user may also wish to determine the appropriate size of one or more surgical instruments to be used during the procedure and/or spinal implants to be implanted. The user may select the "Sizing" tab 216 from the navigation panel on the main tracking screen 200. Based on the clinically significant boundary information explained above, the change in distance along the y axis may indicate implant width, the change in distance along the x axis may indicate implant height, and the change in distance along the z axis may indicate the implant depth as well as instrument depth. The system 10 may provide the user with suggestions for instrument size, implant size, etc. prior to commencing the surgical procedure based on patient size, pathology, and the like.

A scalpel or other instrument is used to make an incision of sufficient size to receive a distal end 224 of the initial dilator 32 at a lateral incision location. The distal end 224 of the initial dilator 32 may be guided through the retroperitoneal space toward the psoas muscle using a fingertip (for example), to protect the peritoneum. The distal end of the initial dilator is then advanced in a substantially lateral direction through the psoas muscle toward the intervertebral disc space at or near the surgical target site. The fibers of the psoas muscle are split using blunt dissection until the spinal target site is reached.

According to some embodiments, the user may track the path of the initial dilator 32 in real time from the incision site to the target spinal site via the instrument tracking mode of the system 10 from the main tracking screen 200. As shown in FIG. 17, the main tracking screen 200 will track the A/P and lateral views of the virtual initial dilator 226 as it advances through the patient to ensure the initial dilator 32 will dock on an ideal location of the psoas muscle prior psoas muscle splitting. In such embodiments, it is to be appreciated that the user need not verify the location of the distal tip of the initial dilator 224 using fluoroscopic imaging, thereby decreasing the exposure to x-ray radiation.

According to some embodiments, the neuromonitoring system 36 may be used to allow for safe passage of the initial dilator 32 through the psoas muscle to the spinal target site. In such embodiments, initial dilator 32 has a proximal end configured to attach to a stimulation connector (e.g. a clip cable) in electrical communication with the neuromonitoring system (not shown) and at least one electrode (not shown) at the distal tip 224 of the initial dilator 32. The stimulation connector is coupled to both the initial dilator 32 and the neuromonitoring system 36 to provide a stimulation signal as the initial dilator 32 is advanced through the psoas muscle.

As the initial dilator 32 is advanced through the psoas muscle to the surgical target site, the electrode located at the distal tip 224 the initial dilator 32 emits one or more stimulation pulses and recording electrodes positioned over muscles innervated by nerves traversing through the psoas registers the presence or absence of a significant EMG response. The neuromonitoring system will continuously search for the stimulus threshold that elicits an EMG response in the myotomes monitored and then reports such thresholds on the display 24. According to preferred embodiments, this may be done with a hunting algorithm that quickly and automatically determines stimulation thresholds. As the initial dilator 32 is advanced through the psoas muscle, the stimulus necessary (i.e. the threshold intensity) to elicit an EMG response will vary with distance from one or more nerves. The neuromonitoring system 36 may then report the relative nerve distance indicated by these threshold intensities to the user by any number of color, graphic, or alpha-numeric indicia. By way of example, the user may be presented with the threshold intensity in units of mA and/or a color associated with the predetermined range in which the determined threshold lies. By way of example only, threshold intensities between 1 mA and 6 mA may also display a red color, threshold intensities between 7 mA and 10 mA may also display a yellow color, and threshold intensities greater than 10 mA may display a green color.

According to one or more preferred embodiments, the system 10 is configured simultaneously track the movement of the initial dilator 32 via virtual initial dilator 226 and display neurophysiologic data as the initial dilator 32 is being advanced through the psoas muscle to the spinal target site. For any given position and orientation of the initial dilator 32, EMG threshold intensity information can be captured and displayed on the virtual fluoroscopic images 178, 184 corresponding to the position and orientation the initial dilator 32 occupied when said threshold intensity was elicited. Thus, the system can map out the location of nearby nerves as the initial dilator 32 is advanced through the psoas muscle to the spinal target site. This may be accomplished by selecting the "Show Nerve Mapping" tab 220 on the main tracking screen 200. Various illustrative embodiments are explained in detail below.

Figure 18:
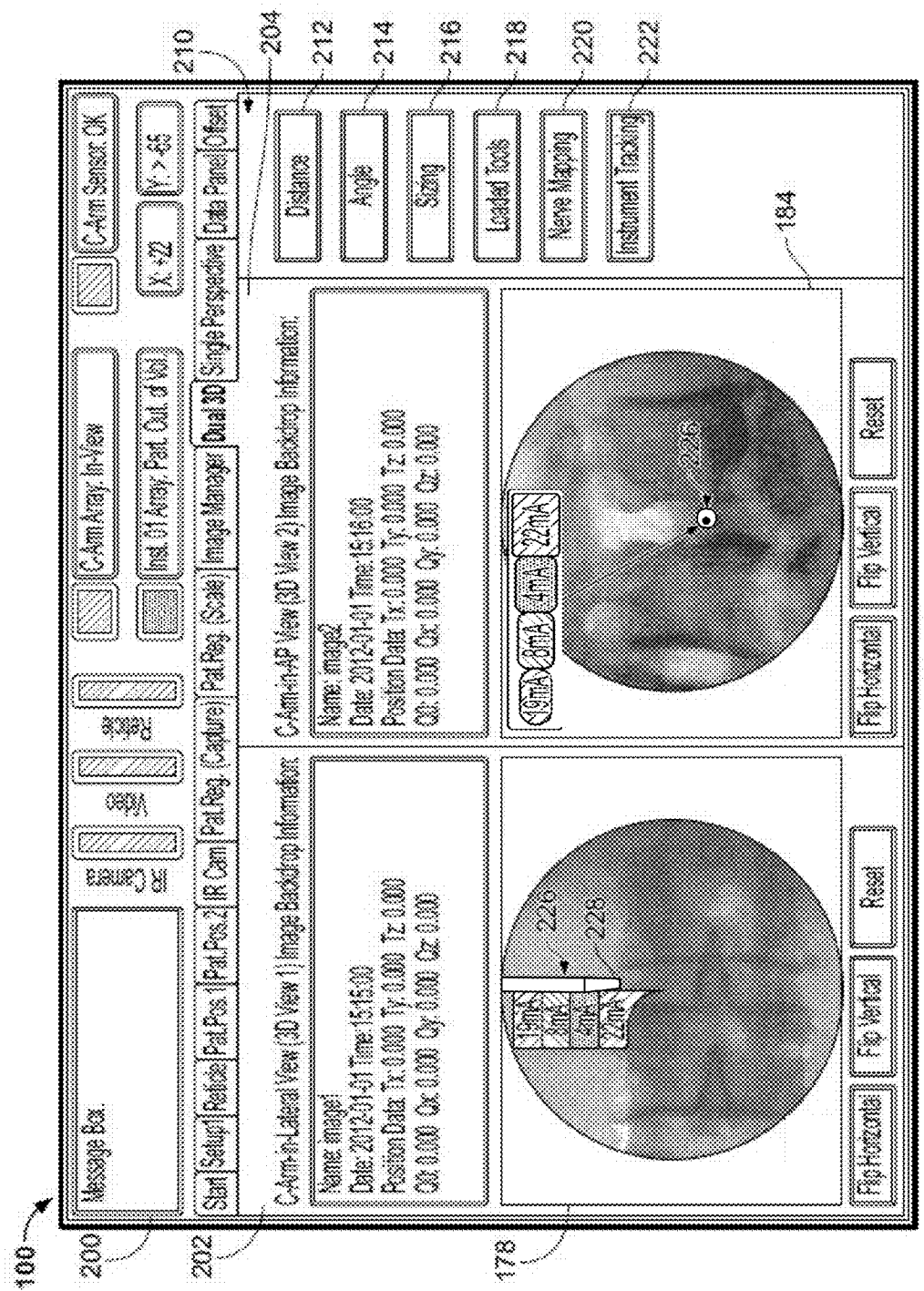
FIG. 18 is a screen shot of the system in nerve mapping mode according to a first embodiment showing neurophysiologic recordings at various depth locations as an initial dilator is advanced from the incision site to a target site on a patient.

In some implementations (illustrated by way of example, in FIG. 18), the position of the initial dilator 32 within the surgical corridor may be tracked as the relative distance of nearby nerves is monitored within the surgical corridor relative to the presence of and indicated via a color (e.g. red/yellow/green) and a number based on the threshold intensities required to elicit a significant threshold response as the initial dilator 32 is advanced to the surgical site. At the same time, the location of the initial dilator 32 (preferably, the distal tip 224) may be tracked on the virtual fluoroscopic images 178, 184 as set forth above (via the virtual distal tip 228 of the virtual initial dilator 226). The system 10 may then map each neurophysiologic response to the precise spatial orientation where each neurophysiologic response was obtained onto the virtual fluoroscopic images 178, 184 as the initial dilator 32 moves towards the spinal target site. As illustrated in FIG. 18, the main tracking screen 200 shows that the neuromonitoring system 36 registered a significant EMG response with 19 mA as the virtual initial dilator 226 was positioned at location 230 (depicted as green on the screen 200), a significant EMG response at 8 mA as the virtual initial dilator 226 advanced to location 232 (depicted as yellow the screen 200), a significant EMG response at 4 mA as the virtual initial 226 dilator advanced to location 234 (depicted as red on the screen 200), and a significant EMG response at 22 mA as the virtual initial dilator 226 advanced to location 236 which is the spinal target site (depicted as green on the screen 200). Armed with this information, the user knows that at least one nerve lies near location 234.

Figure 19:
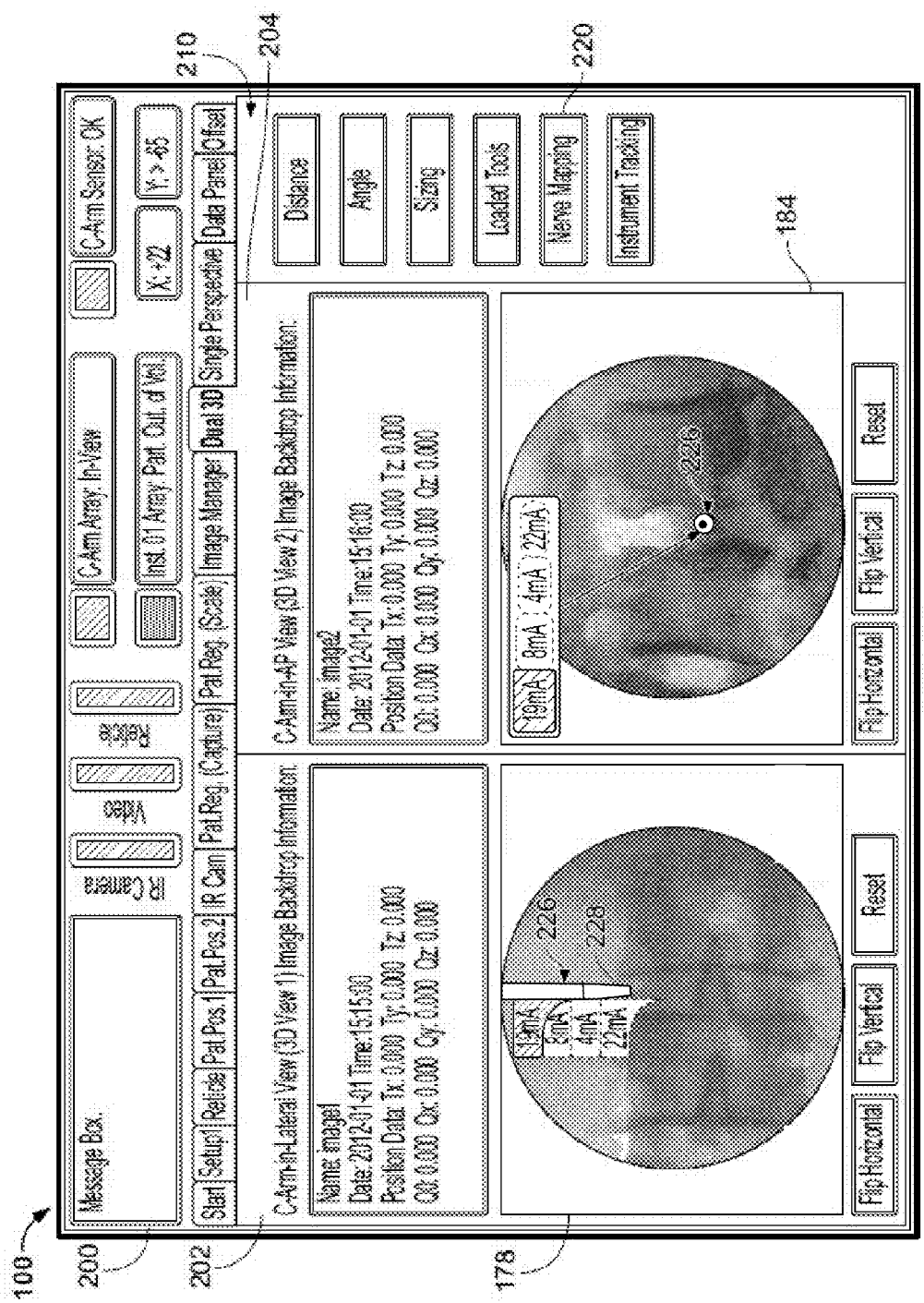
FIG. 19 is a screen shot of the system in nerve mapping mode according to a first embodiment showing neurophysiologic recordings at various depth locations as the initial dilator is retreated towards the incision site.
Figure 20:
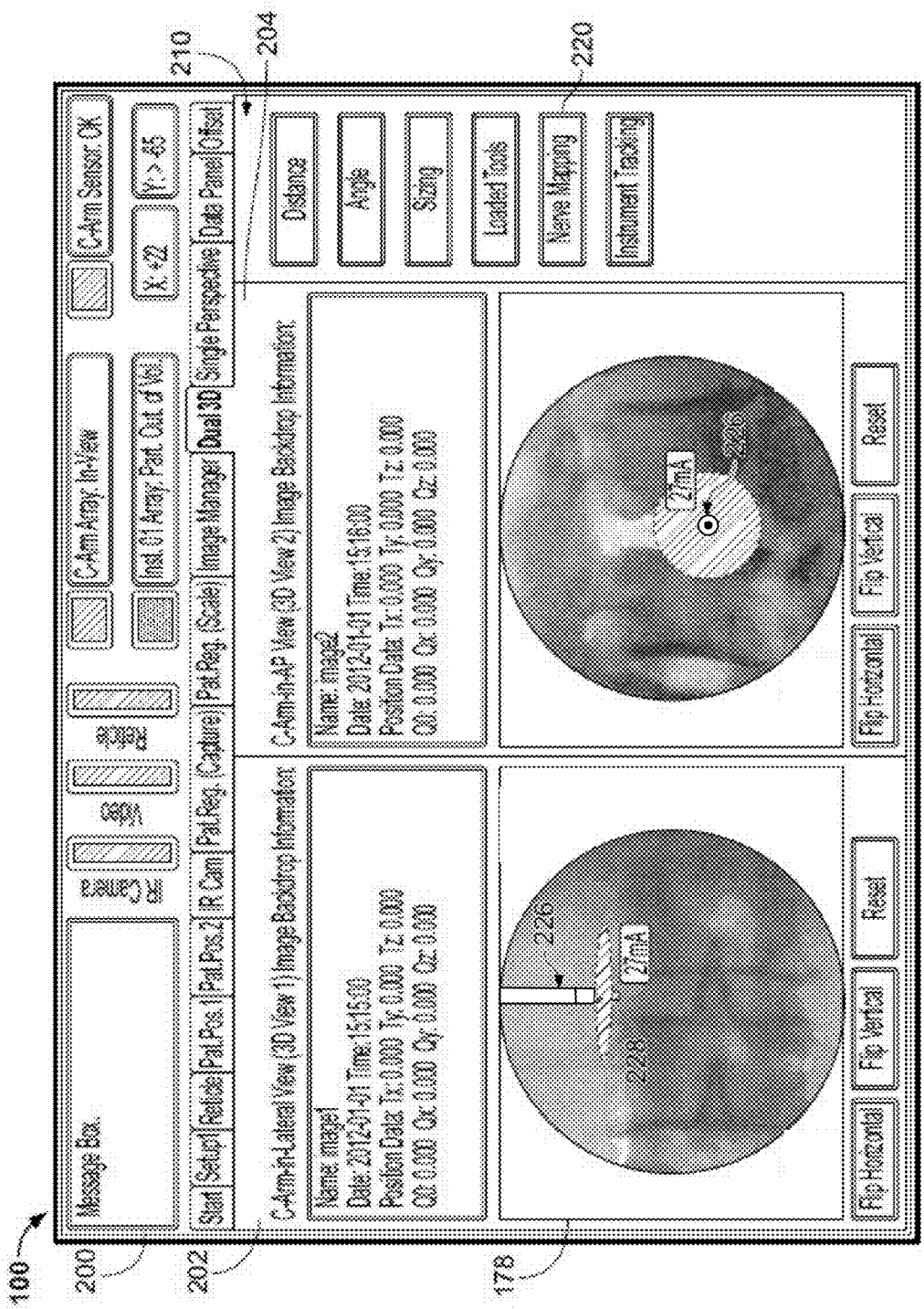
FIGS. 20-23 are screen shots of the system in nerve mapping mode according to a first embodiment showing neurophysiologic recordings at various depth locations and various rotational positions of the electrode as the initial dilator is advanced towards the incision site.

According to one or more implementations, the system 10 not only possesses the capability to register spatial positioning and neurophysiologic responses during advancement of the initial dilator 32, but also spatial positioning and neurophysiologic responses during retreat and/or repositioning of the initial dilator 32. As illustrated in FIG. 19, the main tracking screen 200 shows the virtual initial dilator 226 retreating from the spinal target site (location 236). As the virtual initial dilator 226 retreats, the neurophysiologic responses obtained at locations 236, 234, and 232 are removed (as shown in FIG. 20, the numeric results may be grayed-out and/or with dashed lines). From here, the initial dilator 32 may be repositioned and the repositioned path will be shown with virtual initial dilator 226 along with new neurophysiologic responses as the initial dilator 32 is advanced again.

Neurophysiologic data may also be used to track the orientation of one or more nerves relative to the distal tip 224 of the initial dilator 32. Preferably once the depth of the nerves has been ascertained (as explained above with respect to FIG. 19), the user can track the radial position of the distal electrode (not shown) with neurophysiologic data indicative of the relative radial position of one or more nearby nerves mapped onto the virtual fluoroscopic images 178, 164.

Figure 21:
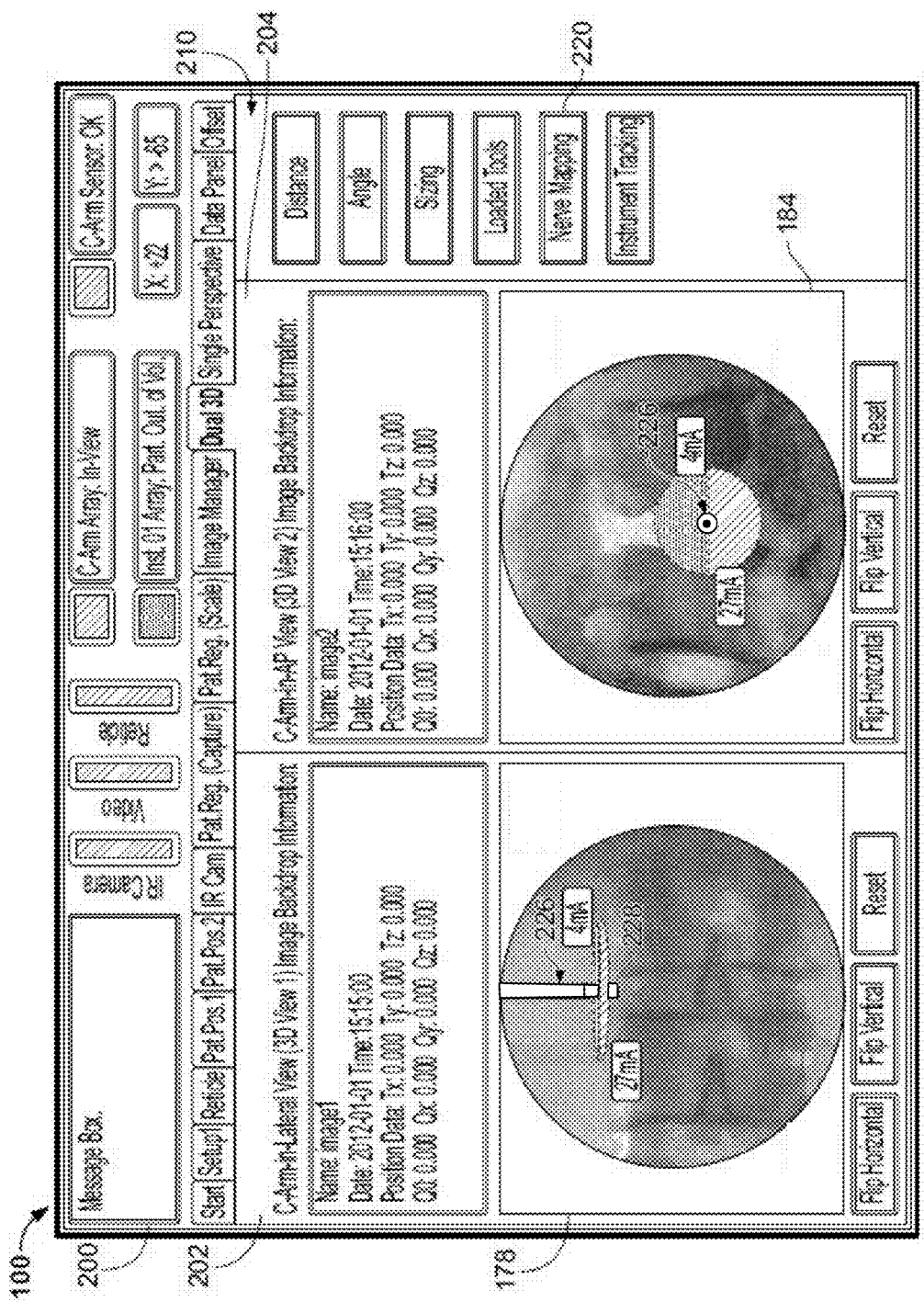
Figure 22:
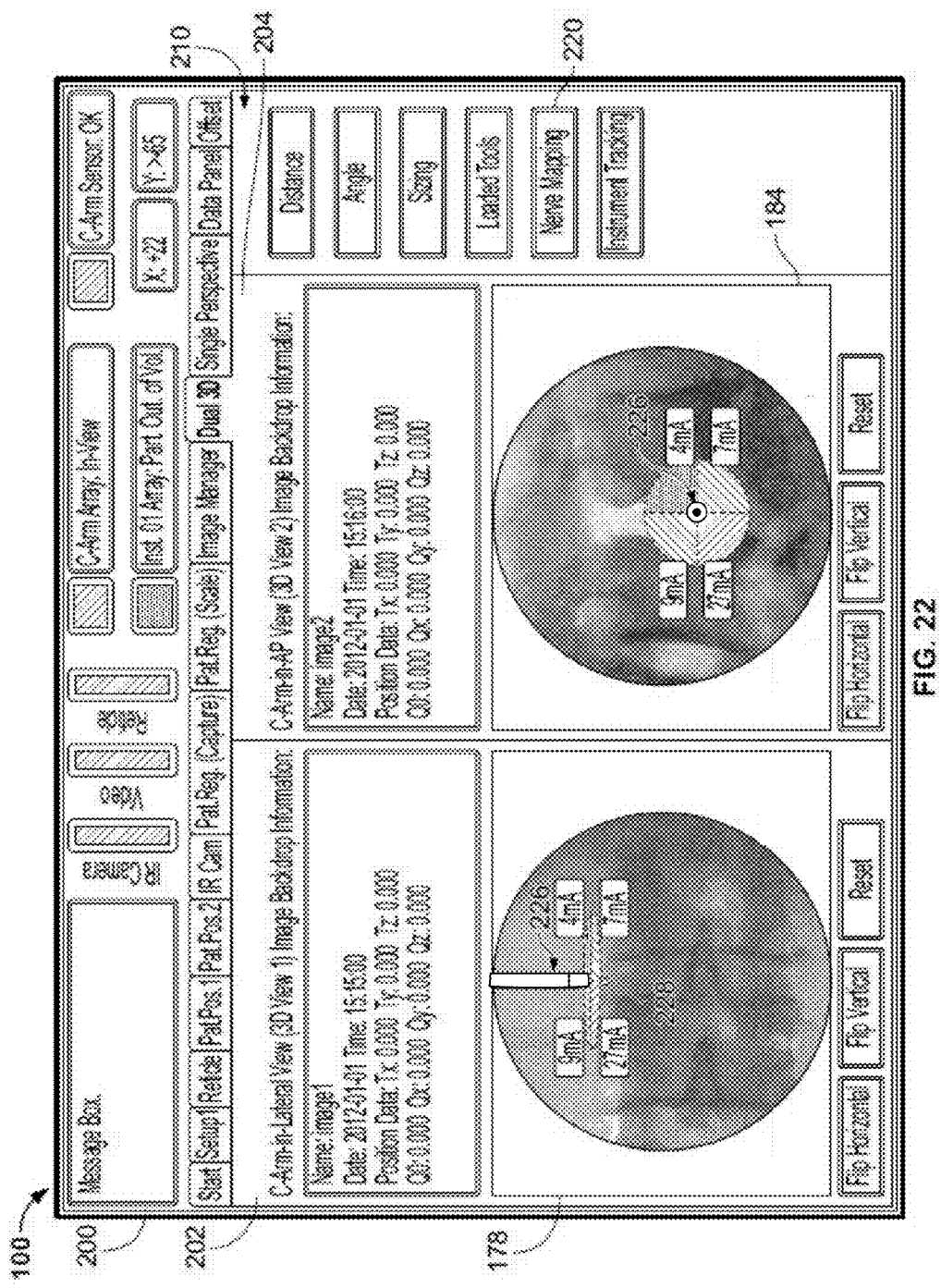
Figure 23:
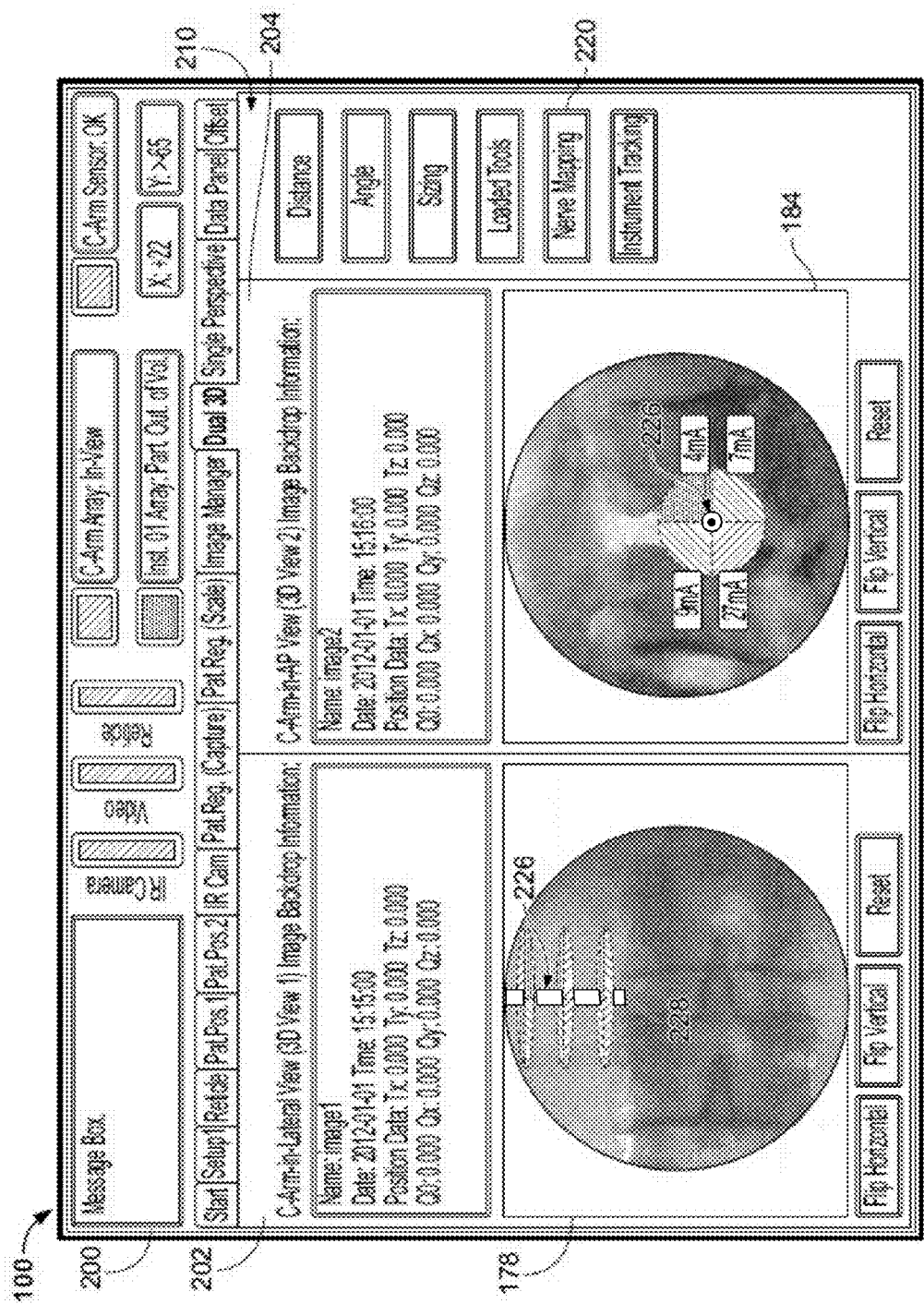
Figure 24:
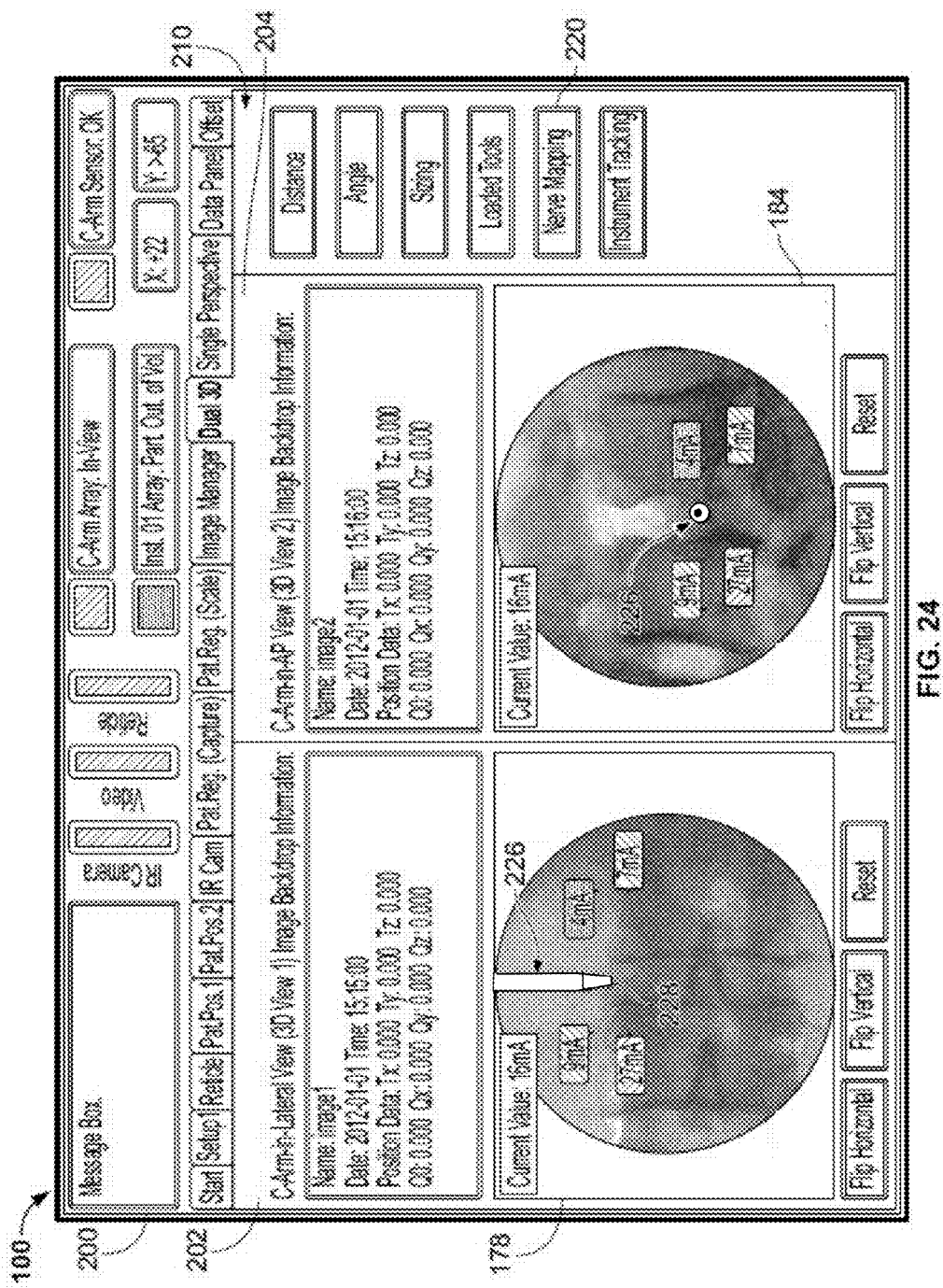
FIG. 24 is a screen shot of the system in nerve mapping mode according to a second embodiment.
Figure 25:
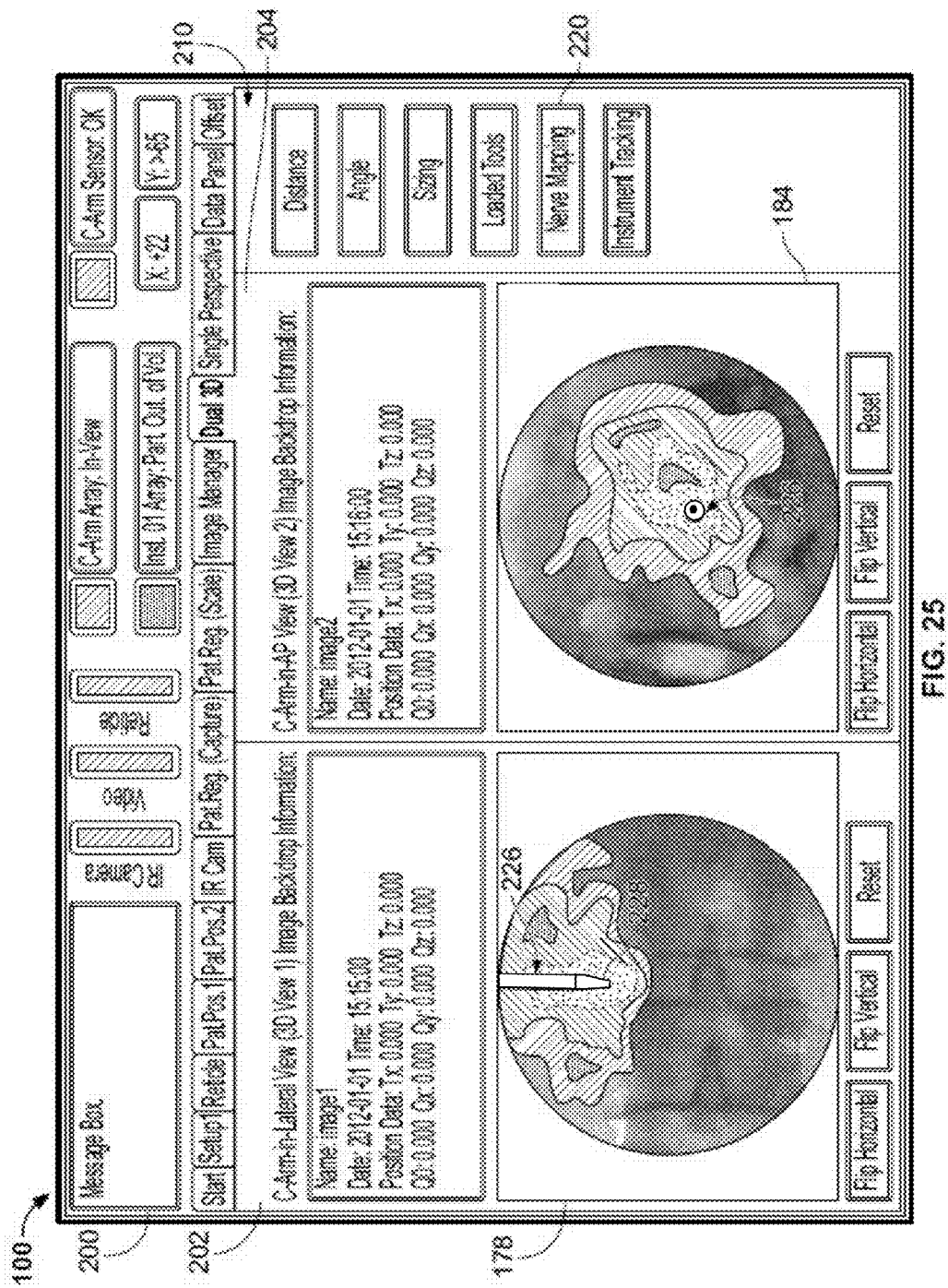
FIG. 25 is a screen shot of the system in nerve mapping mode according to a third embodiment.
Figure 26:
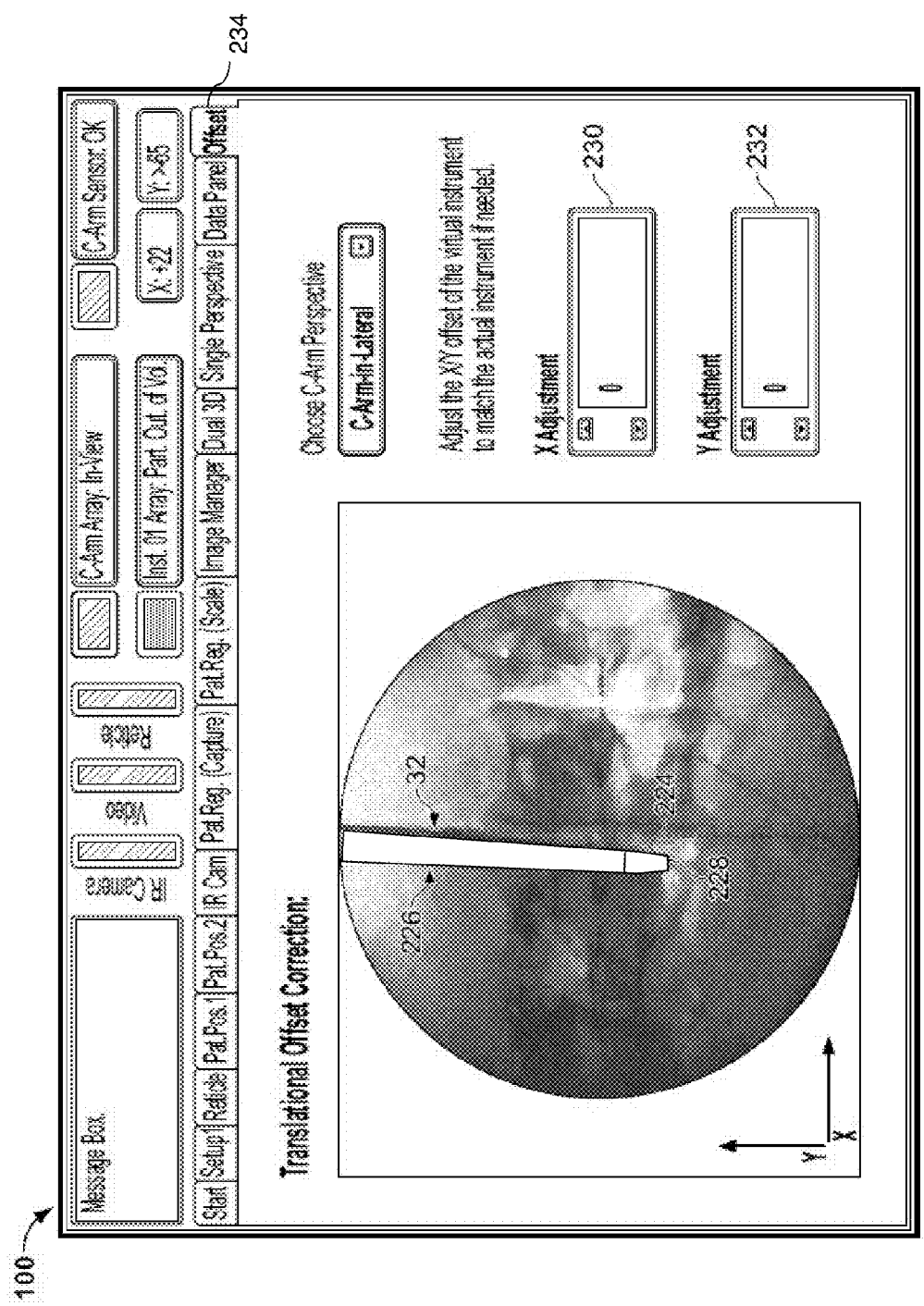
FIG. 26 is a screen shot of the system in offset mode according to a first embodiment.

In some implementations, once the depth has been ascertained (a first discrete position), the surgeon may then rotate the initial dilator 32 (shown as virtual initial dilator 226) about its longitudinal axis through any number of discrete positions and allow the neuromonitoring system 36 to capture neurophysiologic data for each discrete point. FIGS. 20-23 illustrate this concept at one discrete position, two discrete positions, and four discrete positions, respectively. FIG. 20 shows the neurophysiologic data at one discrete point (with no rotation of the initial dilator 32, a first significant neurophysiologic response was obtained at 27 mA (depicted as green on screen 200) which may convey to the user that no nerve lies close to the electrode on the initial dilator 32 at the first discrete position. As shown in FIG. 21, as the user rotates the initial dilator 32 about its longitudinal axis to a second radial position (shown here as 180 degrees from the first discrete point), a second significant neurophysiologic response was obtained at 4 mA (depicted as red on the screen 200) which may convey to the user that at least one nerve lies close to the second discrete position. FIG. 22 shows the initial dilator 32 rotated about its longitudinal axis to four radial positions. Here, as the user rotates the initial dilator 32 about its longitudinal axis approximately 90 degrees from the first discrete position, a second neurophysiologic response was obtained at 7 mA (depicted as yellow on screen 200). As the user rotates the initial dilator 32 about its longitudinal axis approximately 90 degrees from its second discrete position, a third neurophysiologic response was obtained at 4 mA (depicted as red on screen 200). As the user rotates the initial dilator 32 about its longitudinal axis approximately another 90 degrees from its third discrete position, a fourth neurophysiologic response was obtained at 9 mA (depicted as yellow on screen 200). As the user rotates the initial dilator 32 to more radial positions, more refined information as to the exact position of a nearby nerve may be ascertained. It is to be appreciated that the system may be used as frequently as the surgeon wants to allow the system to give the discrete position discrete neurophysiologic data (e.g., minimum of two discrete points, maximum of surgeon preference. Additionally, it is to be appreciated that the system may give the orientation data at multiple depth locations as shown in FIG. 23.

The examples set forth above are illustrative and the system 10 may represent the data differently (e.g. an intensity chart over anatomy (FIG. 24) or a color map (FIG. 25), etc. . . . ). Furthermore, the system 10 may incorporate more data points (e.g., time of the data capture, trend data) that assist the user in integrating the positioning and neurophysiologic mapping into the surgical procedure. While the foregoing was explained with respect to an initial dilator 32, it is contemplated that the virtual image/mapping may be used for subsequent dilators, one or more retractor blades, etc.).

After the initial dilator 32 has docked at the spinal target site, the position of the distal end of the dilator may be confirmed by selecting the "Instrument Tracking" tab 222 and verifying the position of the distal tip 224 of the initial dilator 32 (via the distal tip 228 of the virtual initial dilator 226) is at the spinal target site (thereby obviating the need to confirm this position using fluoroscopic imaging). A K-wire of the initial dilator 32 is then introduced into the targeted disc space after the initial dilator 32 is passed through the psoas muscle. A sequential dilation system including one or more supplemental dilators may be guided over the initial dilator for the purpose of further dilating the tissue down to the surgical target site. It is to be appreciated that each component of the sequential dilation system may be outfitted with an IR-reflective array 16 and its location mapped onto the virtual fluoroscopic image. Also, each component may be outfitted with one or more electrodes such that it neurophysiologic data obtained while each component is advanced to the spinal target site may be mapped onto the virtual fluoroscopic image as well.

The retractor blades of the access system are introduced over the supplemental dilator (or the initial dilator if the sequential dilation system is not employed) toward the disc space. Again, the neuromonitoring system 36 may be used to perform neuromonitoring as the blades are positioned helps provide safe passage through the psoas muscle. In some embodiments, a posterior shim element and/or retractor extenders (not shown) are engaged with the retractor blades. After the retractor blades are introduced along the distraction corridor, the surgical tracking system 10 may be used to confirm the position of the blades proximal to the disc space (again, thereby obviating the need to confirm the position of the blades with fluoroscopic imaging). Once the retractor assembly is fully assembled, the blades may be used to retract the distraction corridor so as to form an operative corridor. Tracking may be used to verify the position of the distal ends of the blades without the need for fluoroscopic imaging.

Various instruments may be inserted through the operative corridor to prepare the targeted disc space. At least one preparation tool such as a disc cutter, pituitary, scrapper, curette, or the like is inserted through the operative corridor to prepare the disc space. Any one of these may be outfitted with an IR-reflective tracking array 20 and its location tracked during the procedure, to verify for the user, for example, the extent of discectomy completed and the extent of discectomy left to be done. Following disc preparation, one or more sizers are inserted into the disc space to provide appropriate disc height restoration. This can also be monitored via position tracking obviating the need for fluoroscopy.

An appropriately-sized implant (preferably determined by using the "Sizing" tab 216 as set forth above) is then advanced into the disc space with an inserter tool. The implant is releasably secured to the inserter tool such that the surgeon may release the implant when it is properly positioned in the disc space.

Particularly in surgical procedures in which more than one spinal level is being operated on, additional fluoroscopic images are traditionally needed to localize the next spinal level (e.g. the superior or inferior spinal level) and to align subsequent fluoroscopic images used in tracking surgical instruments. The system 10 of the present invention may decrease the need for additional fluoroscopic images when transitioning from one spinal level to the next. According to one embodiment, the system 10 may allow the C-arm 26 to be moved during the procedure. As the C-arm is moved from one spinal level to another, the virtual marker (e.g. dot 130) captures the C-arm's 26 current position as it moves up and down or left and right relative to the virtual A/P and lateral fluoroscopic images. The user may then manipulate the C-arm 26 such that the dot 130 aligns with a point of interest at the next spinal level. It is to be appreciated that while this may not obviate the need for ionizing radiation entirely, it allows the user a close approximation of the location of the C-arm 26 without the use of localizing fluoroscopy.

It may also be advantageous for a user to verify that the C-arm 26 is displaying images accurately (i.e. the images are not rotated clockwise or counterclockwise) such that they are inputted into the system 10 accurately. Thus, the system 10 also provides an image rotation feature which verifies and/or corrects the images displayed so that they are accurately displayed with respect to gravity. First, the user takes a fluoroscopic image with an instrument that is known to be positioned vertically with respect to gravity (e.g., a plumb bob, a probe, or instrument with an attached orientation sensor, etc.) which is imported into the system 10. Next, the user takes a fluoroscopic image of the instrument with angular feedback (e.g. a plumb bob, a probe, or an instrument with an attached orientation sensor, etc.) registering at 0°/0° which is also imported into the system 10. If the second image does not appear properly positioned, the image on the system 10 may need to be rotated relative to the screen 100 until the image with the instrument in it does appear properly positioned.

The system 10 of present invention also provides manners in which a user may verify the virtual surgical objects are tracking "true" to the actual surgical object. In some instances, a virtual surgical object may not track "true" if the patient has moved on the surgical table or the image is distorted due to external factors.

According to a first implementation, the user may select the "Offset" mode 230 from the main tracking screen 200 and take a fluoroscopic image with a surgical object positioned within the disc space and compare the fluoroscopic image with the virtual instrument overlaid onto the same fluoroscopic image. If the position of the actual and virtual surgical objects do not align adequately, modifications may be made to the position of the virtual surgical object on the display screen 100. As shown by way of example in FIG. 26, a fluoroscopic image may be taken with the initial dilator 32 positioned within the disc space and the virtual initial dilator 226 projected onto the fluoroscopic image. In this illustration, it can be seen that the two instruments do not line up exactly. The user may instruct the system 10 to make adjustments to the x and y position of the virtual initial dilator 226 to align the virtual tip 228 of the virtual initial dilator 226 with the actual tip 224 of the actual initial dilator 32 using the x and y position adjustment fields 230, 232. In this example, an upward correction in the y direction and a correction to the right in the x direction would realign the virtual initial dilator 226 to the actual initial dilator 32.

According to another implementation, the Offset feature of the surgical tracking system 10 may be used without having to take additional fluoroscopic images during the procedure. By way of example, the user may repeatedly touch a tracked surgical object to a home position (located within the surgical corridor) that is easily identified both by visual identification and on the virtual fluoroscopic and comparing the offset (if any) that the virtual surgical object has relative to the home location. If, for example, the virtual instrument tracks "true", the position of the distal end of the tracked surgical object will appear directly on top of the home position. If however, the virtual instrument no longer tracks "true," the position of the distal end of the tracked instrument may appear offset from the home position. In that case, the user may make adjustments to the virtual surgical object in the x and y directions using the x and y position adjustment fields 230, 232 as explained above. The user can come back to the recorded "home position" as the surgery progresses and verify accurate tracking through the same virtual to real-world comparison multiple times during the surgery if so desired. The home position may be an anatomical landmark (e.g., an ipsilateral osteophyte), a radiolucent marker positioned within the surgical corridor (e.g., a radiolucent sphere) such that a tracked surgical object can be rotated around the sphere's surface and the user can confirm that the movements correlate to the sphere's location and diameter; and a radiodense marker that can be used to produce a definite mark on the virtual fluoroscopic image to confirm that the location of the instrument is on the "home position."

According to yet another implementation, the Offset feature may detect patient movement using accelerometers (such as those disclosed in the '121 application). By way of example, a two- or three-axis accelerometer affixed to the patient in a known position and orientation can be used to alert the user and system 10 of possible patient movement. The accelerometers' measurement of static acceleration provides tilt and orientation information and the accelerometers' measurement of dynamic acceleration provides vibration and other movement information. If significant changes in patient positioning are detected by the accelerometers, the system 10 may display a warning that the tracking accuracy may be decreased such that re-registration and scaling may be advisable.

Details of the surgical tracking system 10 are now discussed in conjunction with a second exemplary use thereof for monitoring the trajectory of a surgical instrument used during pedicle fixation to ensure proper placement of pedicle screws. According to one embodiment, the system 10 may be used in conjunction with, or further integrated with, the surgical trajectory monitoring system of the '121 application.

Prior to forming a pedicle pilot hole or placing pedicle screws (preferably prior to starting the surgical procedure), it may be of interest to capture the starting point and stopping point of the pedicle cannulation using the surgical tracking system 10. With the IR tracking array 16 positioned on the reticle 30, the control unit 22 captures the spatial information of the C-arm 26 at a first spinal level of interest via the IR position sensor 14. A first lateral fluoroscopic image is taken with the lateral start points centered in the center of the image. A second lateral fluoroscopic image is then taken with the lateral stopping points centered in the center of the image. The first lateral image may be used as the lateral virtual backdrop image for that spinal level and scaled as set forth above, with reference to the Points A and B in the lateral, trans-psoas access procedure. According to some implementations, a virtual protractor may be projected off of this lateral backdrop image such that the cranial-caudal angles may be measured and inputted into the system 10 as set forth in the '121 application. Next, a first A/P fluoroscopic image is taken with the left start point centered in the image (for example, the lateral border of the left pedicle). A second A/P fluoroscopic image is taken with the right start point centered in the image (for example, the lateral border of the right pedicle). The first A/P image may be used as the A/P virtual backdrop image for that spinal level and scaled as set forth above, with reference to the Points A' and B' in the lateral, trans-psoas access procedure. It is to be appreciated that selecting the ideal start and stop points for pedicle cannulation in this way is advantageous for at least two reasons. First, fluoroscopic radiation to transition to this spinal level during the procedure is eliminated because the system 10 will alert the user when the C-arm 26 has been brought into the correct position. Second, fluoroscopic radiation is reduced when transitioning between lateral and A/P images. Aside from acquiring the starting points, no further imaging is required.

During the procedure, a surgical instrument may be advanced to the target site and positioned on the lateral margin of the pedicle, the preferred starting point according to the embodiment set forth above. By way of example only, the surgical instrument is the pedicle access probe including the orientation sensor described in the '121 application and further outfitted with an IR tracking array 20. As the depth of the pedicle access probe is penetrated deeper into the pedicle, its location does not need to be checked via fluoroscopic radiation. Instead, the location of the pedicle access probe may be projected onto the screen 100 in both the lateral and A/P views via a virtual pedicle access probe (not shown). According to some implementations, the neuromonitoring system 36 may provide neurophysiologic data and/or mapping during pedicle cannulation. Thus, the system 10 can show the dynamic relation of the distal tip of the pedicle access probe relative to the medial pedicle wall and the depth within the vertebral body via the virtual pedicle access probe instead of relying on fluoroscopic imaging.

While the invention is susceptible to various modifications and alternative forms, specific embodiments thereof have been shown, by way of example only, in the drawings and are herein described in detail. It should be understood, however, that the description herein of specific embodiments is not intended to limit the invention to the particular forms disclosed. On the contrary, the invention is to cover all modifications, equivalents, and alternatives falling within the spirit and scope of the invention as defined herein.

What is claimed is:

1. A method for tracking a position of an instrument relative to a surgical target site, said method comprising the steps of:
   using an imaging device to take a first image of a patient's body in a first anatomical view, wherein said imaging device displays a virtual center location when taking said first image and said first image has a user defined first point location at said virtual center location, and wherein said imaging device is in a first position;
   obtaining three-dimensional positional data of the location of said imaging device in said first position while taking said first image;
   using said imaging device to take a second image of said patient's body in said first anatomical view, wherein said imaging device displays a second virtual center location when taking said second image and said second image has a user defined second point location at said second virtual center location, and wherein said imaging device is in a second position, and wherein movement between said first and second positions of said imaging device is constrained to one axis;
   obtaining three-dimensional positional data of the location of said imaging device in said second position while taking said second image;
   scaling the first and second images to create a virtual backdrop image in said first anatomical view for viewing on a display unit, wherein said scaling comprises selecting the user defined first and second point locations to calculate a physical distance between said user defined first and second point locations and selecting at least one said user defined first and second point locations from at least one of said first and second images to correlate said physical distance between said user defined first and second point locations on said patient's body and a number of pixels between said user defined first and second point locations as represented on said display unit; and
   monitoring three-dimensional position data of at least one surgical instrument via said display unit as said surgical instrument is moved within said patient's body by tracking a virtual representation of said surgical instrument overlaid onto said virtual backdrop image.

2. The method of claim 1, wherein said imaging device is a c-arm fluoroscope.

3. The method of claim 1, wherein said user defined first point location is on the spine of said patient.

4. The method of claim 1, wherein said first anatomical view is at least one of a lateral view and an anterior-posterior view.

5. The method of claim 1, wherein said three-dimensional positional data of the first and second positions of the imaging device is registered using an infrared position tracking system.

6. The method of claim 1, wherein said user defined second point location is on the spine of said patient.

7. The method of claim 1, wherein the scaling is accomplished manually.

8. The method of claim 1, wherein the at least one surgical instrument comprises at least one of a cannula, a dilator, a retractor blade, a k-wire, a cobb, a rasp, a drill, a tap, and a screw driver.

9. The method of claim 1, wherein the position of said at least one surgical instrument is monitored during a spine surgery procedure.

10. The method of claim 9, wherein the spinal surgery procedure is a lateral lumbar spinal surgery procedure.

11. A method for tracking a position of a surgical instrument during a surgical procedure, said method comprising the steps of:
using an intraoperative imaging device in a first position to generate a first radiographic image of a patient's body in a first anatomical view, wherein said first radiographic image displays a first user defined point location in the center of the first image;
using said intraoperative imaging device in a second position to generate a second radiographic image of the patient's body in said first anatomical view, wherein said second radiographic image displays a second user defined point location in the center of the second image;
obtaining three-dimensional positional data of said first position of said imaging device during generation of said first image and said second position of said imaging device during generation of said second image;
scaling the first and second images to create a first virtual backdrop image in said first anatomical view for viewing on a display unit, said scaling step comprising correlating a physical distance between the first and second user defined point locations on said patient's body and a number of pixels between said first and second user defined point locations as represented on said display unit;
using said imaging device in a third position to generate a third radiographic image of the patient's body in a second anatomical view, wherein said third radiographic image displays a third user defined point location in the center of the third image;
using said imaging device in a fourth position to generate a fourth radiographic image of the patient's body in said second anatomical view, wherein said fourth radiographic image displays a fourth user defined point location in the center of the fourth image;
obtaining three-dimensional positional data of said third position of said imaging device during generation of said third image and said fourth position of said imaging device during generation of said fourth image;
scaling the third and fourth images to create a second virtual backdrop image in said second anatomical view for viewing on said display unit, said scaling the third and fourth images step comprising correlating a physical distance between the third and fourth user defined point locations on said patient's body and a number of pixels between said third and fourth user defined point locations as represented on said display unit; and
tracking a virtual representation of a surgical instrument against said first and second virtual backdrop images as the actual surgical instrument is moved within said patient's body.

12. The method of claim 11, wherein said imaging device is a c-arm fluoroscope.

13. The method of claim 11, wherein said three-dimensional positional data of the first, second, third, and fourth positions of the imaging device is registered using an infrared position tracking system.

14. The method of claim 11, wherein said first and second anatomical views are anterior-posterior and lateral views.

15. The method of claim 11, wherein the surgical instrument is at least one of an intervertebral implant, an intervertebral trial, a rasp, a cobb, a retractor, a dilator, a cannula, a k-wire, a drill, a tap, and a screw driver.

16. The method of claim 11, wherein each said scaling step is accomplished manually.

17. The method of claim 11, wherein the position of said surgical instrument is monitored during a spine surgery procedure.

18. The method of claim 17, wherein the spinal surgery procedure is a lateral lumbar spinal surgery procedure.

* * * * *